United States Patent
Zhao et al.

(10) Patent No.: US 10,234,402 B2
(45) Date of Patent: Mar. 19, 2019

(54) SYSTEMS AND METHODS FOR DEFECT MATERIAL CLASSIFICATION

(71) Applicant: KLA-Tencor Corporation, Milpitas, CA (US)

(72) Inventors: Guoheng Zhao, Palo Alto, CA (US); J. K. Leong, San Jose, CA (US); Michael Kirk, Los Altos Hills, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 10 days.

(21) Appl. No.: 15/480,206

(22) Filed: Apr. 5, 2017

(65) Prior Publication Data

US 2018/0188188 A1 Jul. 5, 2018

Related U.S. Application Data

(60) Provisional application No. 62/442,838, filed on Jan. 5, 2017.

(51) Int. Cl.
  *G01N 21/00* (2006.01)
  *G01N 21/95* (2006.01)
  (Continued)

(52) U.S. Cl.
  CPC ....... *G01N 21/9505* (2013.01); *G01N 21/643* (2013.01); *G01N 21/6445* (2013.01);
  (Continued)

(58) Field of Classification Search
  CPC ....... G01N 21/9501; G01N 2021/8854; G01N 2021/8822; G01N 2021/8825;
  (Continued)

(56) References Cited

U.S. PATENT DOCUMENTS

| 5,037,202 A | 8/1991 | Batchelder et al. |
| 5,923,430 A | 7/1999 | Worster et al. |

(Continued)

FOREIGN PATENT DOCUMENTS

| JP | 2016020867 A | 2/2016 |
| WO | 2000070646 A1 | 11/2000 |
| WO | 2015058702 A1 | 4/2015 |

OTHER PUBLICATIONS

International Search Report dated Apr. 24, 2018 for PCT/US2018/012103.

*Primary Examiner* — Hoa Q Pham
(74) *Attorney, Agent, or Firm* — Suiter Swantz pc llo

(57) ABSTRACT

A inspection system includes an illumination source to generate an illumination beam, focusing elements to direct the illumination beam to a sample, a detector, collection elements configured to direct radiation emanating from the sample to the detector, a detection mode control device to image the sample in two or more detection modes such that the detector generates two or more collection signals based on the two or more detection modes, and a controller. Radiation emanating from the sample includes at least radiation specularly reflected by the sample and radiation scattered by the sample. The controller determines defect scattering characteristics associated with radiation scattered by defects on the sample based on the two or more collection signals. The controller also classifies the one or more particles according to a set of predetermined defect classifications based on the one or more defect scattering characteristics.

29 Claims, 11 Drawing Sheets

(51) Int. Cl.
*G01N 21/94* (2006.01)
*G01N 21/64* (2006.01)
*G01N 21/88* (2006.01)

(52) U.S. Cl.
CPC ......... *G01N 21/8806* (2013.01); *G01N 21/94* (2013.01); *G01N 21/9501* (2013.01); *G01N 2021/646* (2013.01); *G01N 2021/8825* (2013.01); *G01N 2021/8854* (2013.01)

(58) Field of Classification Search
CPC ... G01N 2201/06113; G01N 21/95607; G01N 2201/0662; G06T 2207/30148; G06T 7/0002
USPC .......................................... 356/237.1–237.5
See application file for complete search history.

(56) References Cited

U.S. PATENT DOCUMENTS

| | | | |
|---|---|---|---|
| 6,067,154 A | 5/2000 | Hossain et al. | |
| 6,091,493 A | 7/2000 | Stover et al. | |
| 6,122,047 A | 9/2000 | Stover et al. | |
| 6,169,601 B1 | 1/2001 | Eremin et al. | |
| 6,407,386 B1 | 6/2002 | Dotan et al. | |
| 6,440,615 B1 | 8/2002 | Shimizu | |
| 6,486,946 B1 | 11/2002 | Stover et al. | |
| 6,515,742 B1 | 2/2003 | Ruprecht | |
| 6,760,100 B2 | 7/2004 | Ivakhnenko et al. | |
| 6,791,099 B2 | 9/2004 | Some et al. | |
| 7,069,155 B1 | 6/2006 | Phan et al. | |
| 7,295,303 B1 | 11/2007 | Vaez-Iravani et al. | |
| 7,304,310 B1* | 12/2007 | Shortt ................ G01N 21/94 250/372 |
| 7,433,034 B1 | 10/2008 | Huang | |
| 8,073,099 B2 | 12/2011 | Niu et al. | |
| 8,338,194 B2 | 12/2012 | Hesse et al. | |
| 8,823,935 B1 | 9/2014 | Meeks et al. | |
| 9,007,581 B2 | 4/2015 | Horai et al. | |
| 9,234,856 B2 | 1/2016 | Mukaide | |
| 2002/0054291 A1* | 5/2002 | Tsai ................ G01N 21/8806 356/394 |
| 2003/0094586 A1* | 5/2003 | Kurosawa .......... G01N 21/9501 250/559.4 |
| 2006/0159330 A1* | 7/2006 | Sakai .................. G06T 7/001 382/141 |
| 2011/0181868 A1* | 7/2011 | Stokowski ............ B82Y 10/00 356/51 |
| 2013/0107248 A1 | 5/2013 | Wu et al. | |
| 2015/0260659 A1* | 9/2015 | Chuang ............ H01L 27/14609 250/370.08 |
| 2016/0111307 A1 | 4/2016 | Davis | |
| 2016/0123898 A1* | 5/2016 | Chen ................ G01N 21/9501 356/237.5 |
| 2016/0377548 A1 | 12/2016 | Sappey | |

\* cited by examiner

SYSTEMS AND METHODS FOR DEFECT MATERIAL CLASSIFICATION

CROSS-REFERENCE TO RELATED APPLICATION

The present application claims the benefit under 35 U.S.C. § 119(e) of U.S. Provisional Application Ser. No. 62/442,838, filed Jan. 5, 2017, entitled DEFECT MATERIAL CLASSIFICATION, naming Guoheng Zhao, J. K. Leong, and Mike Kirk as inventors, which is incorporated herein by reference in the entirety.

TECHNICAL FIELD

The present disclosure relates generally to defect material classification, and more particularly, to classifying defect materials based on defect scattering characteristics.

BACKGROUND

Semiconductor production environments are typically highly controlled to suppress contamination of wafers with foreign materials that may interfere with the fabrication process or degrade the performance of fabricated devices. Inspection systems are commonly used to locate defects such as, but not limited to, foreign particles on a substrate for screening and avoidance measures. For example, unprocessed wafers may be screened prior to production to select only suitable wafers or to identify defect sites on wafers for production. It may additionally be desirable to classify the material composition of identified defects to determine appropriate cleaning or avoidance steps throughout the fabrication process. However, decreases in the size of fabricated features drive a need to detect and classify ever smaller defects on substrates, which may present challenges for sensitivity and throughput of inspection systems. Therefore, there exists a critical need to develop systems and methods to detect small particles in wafer inspection systems.

SUMMARY

An inspection system is disclosed in accordance with one or more illustrative embodiments of the present disclosure. In one illustrative embodiment, the system includes an illumination source to generate an illumination beam. In another illustrative embodiment, the system includes one or more focusing elements to direct the illumination beam to a sample. In another illustrative embodiment, the system includes a detector. In another illustrative embodiment, the system includes one or more collection elements configured to direct radiation emanating from the sample to the detector. In another illustrative embodiment, the radiation emanating from the sample includes radiation specularly reflected by the sample and radiation scattered by the sample. In another illustrative embodiment, the system includes a detection mode control device to image the sample in two or more detection modes such that the detector generates two or more collection signals based on the two or more detection modes. In another illustrative embodiment, the system includes a controller. In another illustrative embodiment, the controller determines one or more defect scattering characteristics associated with radiation scattered by one or more defects on the sample based on the two or more collection signals. In another illustrative embodiment, the one or more defect scattering characteristics include at least one of a scattering phase, a scattering intensity, or a defect absorption. In another illustrative embodiment, the controller classifies the one or more defects according to a set of predetermined defect classifications based on the one or more defect scattering characteristics.

An inspection system is disclosed in accordance with one or more illustrative embodiments of the present disclosure. In one illustrative embodiment, the system includes an illumination source to generate an illumination beam. In another illustrative embodiment, the system includes one or more focusing elements configured to direct the illumination beam to a sample. In another illustrative embodiment, the system includes a detector. In another illustrative embodiment, the system includes one or more collection elements to direct radiation emanating from the sample to the detector. In another illustrative embodiment, the radiation emanating from the sample includes radiation specularly reflected by the sample and radiation scattered by the sample. In another illustrative embodiment, the system includes a phase control device to introduce two or more different selected phase offsets between the radiation specularly reflected by the sample and the radiation scattered by the sample such that the detector generates two or more collection signals. In another illustrative embodiment, the system includes a controller. In another illustrative embodiment, the controller determines one or more scattering phase values introduced to the illumination beam scattered by one or more defects on the sample based on the two or more collection signals. In another illustrative embodiment, the controller classifies the one or more defects according to a set of predetermined defect classifications based on the one or more scattering phase values.

An inspection system is disclosed in accordance with one or more illustrative embodiments of the present disclosure. In one illustrative embodiment, the system includes an illumination source to generate an illumination beam. In another illustrative embodiment, the system includes one or more focusing elements to direct the illumination beam to a sample. In another illustrative embodiment, the system includes a detector. In another illustrative embodiment, the system includes one or more collection elements to direct radiation emanating from the sample to the detector. In another illustrative embodiment, the radiation emanating from the sample includes radiation specularly reflected by the sample and radiation scattered by the sample. In another illustrative embodiment, the system includes a detection mode control device configured to sequentially create a dry image on the detector as a dry collection signal based on the radiation emanating from the sample and a water immersion image on the detector as an immersion collection signal based on the radiation emanating from the sample contained in an immersion device. In another illustrative embodiment, the system includes a controller. In another illustrative embodiment, the controller compares the dry collection signal and the immersion collection signal to detect one or more defects on the sample. In another illustrative embodiment, the controller classifies the one or more defects according to a set of predetermined defect classifications based on the comparison of the dry collection signal and the immersion collection signal.

A method for defect classification is disclosed in accordance with one or more illustrative embodiments of the present disclosure. In one illustrative embodiment, the method includes illuminating a sample with an illumination beam. In another illustrative embodiment, the method includes collecting illumination emanating from the sample using two or more detection modes to generate two or more collection signals. In another illustrative embodiment, the radiation emanating from the sample includes radiation specularly reflected from the sample and radiation scattered from the sample. In another illustrative embodiment, the method includes determining one or more defect scattering characteristics associated with radiation emanating from one or more defects on the sample based on the two or more collection signals. In another illustrative embodiment, the one or more defect scattering characteristics include at least one of a scattering phase, a scattering intensity, or a defect absorption. In another illustrative embodiment, the method includes classifying the one or more defects according to a selected set of predetermined defect classifications based on the one or more defect scattering characteristics.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which.

DETAILED DESCRIPTION

Figure 1A:
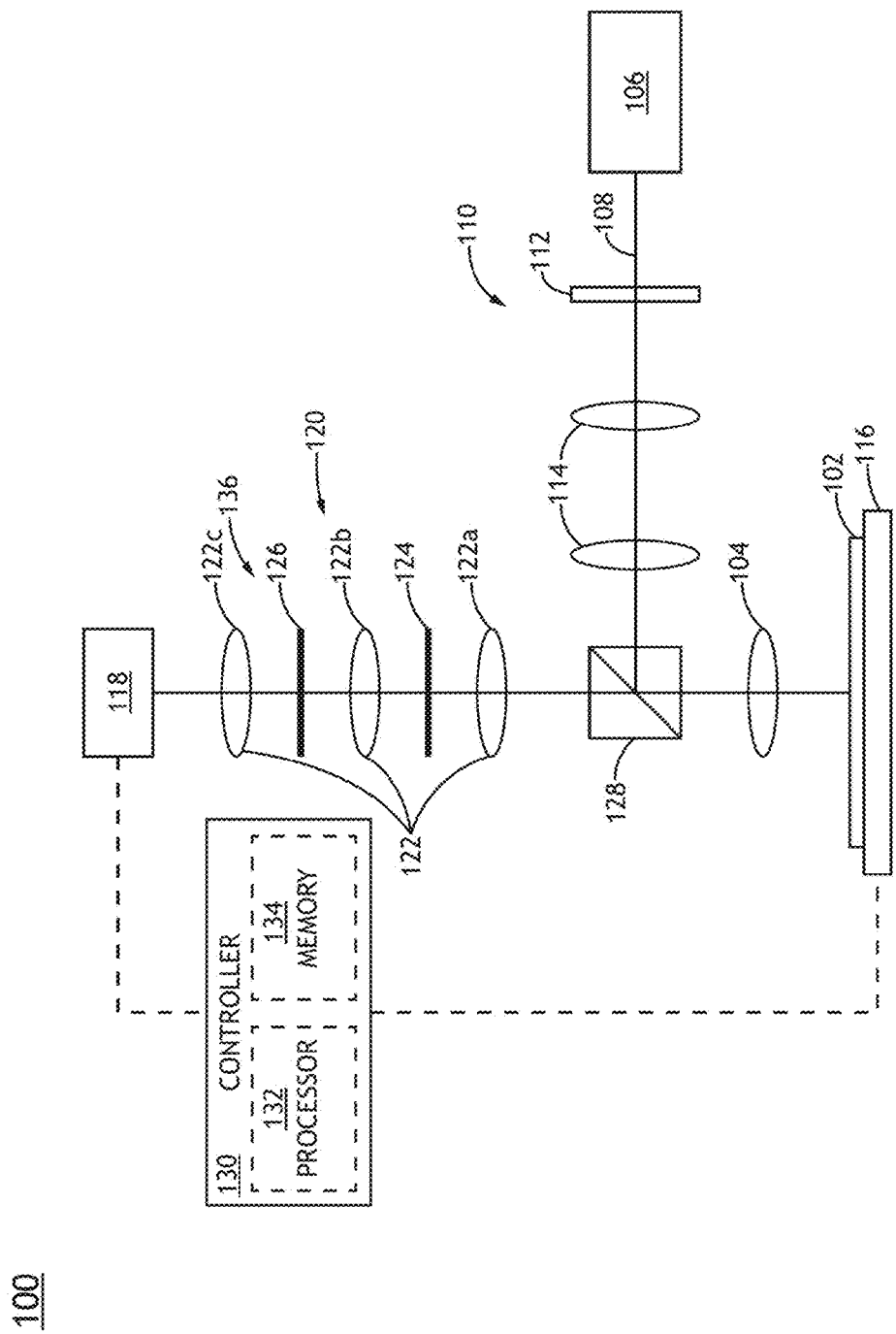
FIG. 1A is a conceptual view of an inspection system configured for illumination of a sample and collection of radiation emanating from the sample with a common objective lens, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Referring generally to FIGS. 1A through 8. Embodiments of the present disclosure are directed to systems and methods for defect detection and classification based on defect scattering characteristics. Generally, defects may exhibit particle scattering characteristics that differ from the surrounding substrate. Accordingly, defects may be classified based on differences in scattering characteristics including, but not limited to, scattering phase, scattering power, or defect absorption. Additional embodiments are directed to measuring defect scattering characteristics by analyzing the interference of radiation reflected by the sample and radiation scattered by the sample. Additional embodiments are directed to measuring defect scattering characteristics by imaging the sample in a series of detection modes designed to distinguish the particle scattering characteristics associated with different material types. For example, defect scattering characteristics may be measured using phase shifting phase contrast imaging. By way of another example, a bright-field image of the sample may provide defect absorption data, while a dark-field image of the sample may provide particle scattering data. Accordingly, a comparison of a bright-field image and a dark-field image of the sample may provide particle scattering characteristics for the detection and classification of defects on the sample. By way of an additional example, scattering cross-sections of different material types may vary based on the immersion medium surrounding the sample such that a comparison of images of the sample may be taken with different immersion media (e.g., water immersion, oil immersion, or the like). Such measurements may thus reveal particle scattering characteristics for defect detection and classification.

The drive to fabricate ever smaller semiconductor devices leads to increasing demands on the uniformity and cleanliness of substrates. The tolerance to which a semiconductor wafer must be free of defects scales with the size of fabricated devices. Inspection systems are typically utilized in semiconductor production environments to detect and/or classify defects such as foreign materials and/or structural defects such as, but not limited to, point defects or line defects. In a general sense, an inspection system may detect any type of defect on a sample at any point in a production process. For example, an inspection system may characterize unprocessed wafers prior to production to select only suitable wafers or to identify defect sites on wafers for production. Further, it may be desirable to classify the material composition of identified defects such that appropriate cleaning or avoidance steps may be taken throughout the fabrication process. Embodiments of the present disclosure are directed to systems and methods for simultaneous detection and classification of the material composition of the defects on a sample.

As used throughout the present disclosure, the term "sample" generally refers to a substrate formed of a semiconductor or non-semiconductor material (e.g. a wafer, or the like). For example, a semiconductor or non-semiconductor material may include, but is not limited to, monocrystalline silicon, gallium arsenide, and indium phosphide. Further, for the purposes of the present disclosure, the term sample and wafer should be interpreted as interchangeable.

It is recognized herein that defect classification may present challenges with respect to sensitivity to small particles as well as throughput. For example, Energy-Dispersive X-Ray Spectrometry (EDX) may provide sensitive defect material analysis capabilities for some materials, but may have an unsuitably slow throughput and may not be suitable for inorganic compounds or organic particles. The use of EDX in a scanning electron microscope is generally described in U.S. Pat. No. 6,407,386, which is incorporated herein by reference in its entirety. By way of another example, Nomarski interferometry may provide the refractive index of particles based on measurements of the attenuation and phase change of a focused laser beam specularly reflected by a sample, but provides low signal on small particles with low specular reflection. The use of Nomarski interferometry for refractive index determination is generally described in M. A. Taubenblatt & J. S. Batchelder, *Applied Optics* 30 (33), 4972 (1991), which is incorporated herein by reference in its entirety.

It may be desirable to utilize scattered light to detect and/or classify defects, particularly for, but not limited to, small particles. However, such methods may also present challenges with respect to sensitivity or illumination requirements. For example, Raman spectroscopy may provide material classification based on the excitation of vibrational modes that manifest as a material-dependent shift (e.g., a Raman shift) between the wavelength of incident illumination and inelastically scattered illumination. However, the signal strength of Raman spectroscopy is proportional to the degree to which excited vibrational modes affect the polarizability of the material such that pure metals may not be detected without an oxidation step. Further, Raman scattering is relatively weak (e.g., relative to elastic Rayleigh scattering) such that long signal integration times limit the usefulness of the technique for small particles. Raman spectroscopy is generally described in Andres Cantanaro, *Procedia Materials Science* 9, 113-122 (2015), which is incorporated herein by reference in its entirety. By way of another example, scattering spectroscopy may provide material properties from scattering power as a function of wavelength. A large range of wavelength differences is typically required to extract material properties, however, particle scattering scales inversely with wavelength (as $\lambda^{-4}$). Therefore, the sensitivity to smaller particles may be limited by the longest wavelength of the illumination source.

Embodiments of the present disclosure are directed to detecting and classifying defects based on defect scattering characteristics such as, but not limited to, the scattering phase associated with illumination scattered by defects, the intensity of illumination scattered by defects, or the absorption of illumination by defects. Further embodiments of the present disclosure are directed to measuring the defect scattering characteristics using a narrowband illumination source. It is recognized herein that the use of a narrowband illumination source may facilitate high sensitivity of both defect detection and classification through efficient scattering of short-wavelength illumination as well as efficient utilization of spectral energy from the illumination source. Accordingly, embodiments of the present disclosure may facilitate sensitive detection and classification of defects including, but not limited to, small particles with a high throughput suitable for use in a fabrication environment.

FIGS. 1A through 1F include conceptual views of an inspection system 100 for detecting and/or classifying defects based on defect scattering, in accordance with one or more embodiments of the present disclosure.

FIG. 1A is a conceptual view of an inspection system 100 configured for illumination of a sample 102 and collection of radiation emanating from the sample 102 with a common objective lens 104, in accordance with one or more embodiments of the present disclosure.

In one embodiment, the inspection system 100 includes an illumination source 106 configured to generate at least one illumination beam 108. The illumination beam 108 may include one or more selected wavelengths of light including, but not limited to, vacuum ultraviolet (VUV) radiation, deep ultraviolet (DUV) radiation, ultraviolet (UV) radiation, visible radiation, or infrared (IR) radiation. The illumination source 106 may include, but is not limited to, a monochromatic light source (e.g. a laser), a polychromatic light source with a spectrum including two or more discrete wavelengths, a broadband light source, or a wavelength-sweeping light source. Further, the illumination source 106 may be, but is not required to be, formed from a white light source (e.g. a broadband light source with a spectrum including visible wavelengths), a laser source, a free-form illumination source, a single-pole illumination source, a multi-pole illumination source, an arc lamp, an electrode-less lamp, or a laser sustained plasma (LSP) source.

In another embodiment, the spectrum of the illumination beam 108 is tunable. In this regard, the wavelengths of radiation of the illumination beam 108 may be adjusted to any selected wavelength of radiation (e.g. UV radiation, visible radiation, infrared radiation, or the like).

In another embodiment, the illumination source 106 directs the illumination beam 108 to the sample along an illumination pathway 110. The illumination pathway 110 may include one or more beam conditioning elements 112 for modifying and/or conditioning the illumination beam 108. For example, the beam conditioning elements 112 may include, but are not limited to, polarizers, filters, beam splitters, diffusers, homogenizers, apodizers, or beam shapers. The illumination pathway 110 may also include one or more illumination pathway lenses 114 for controlling one or more characteristics of the illumination beam 108. For example, the one or more illumination pathway lenses 114 may provide an optical relay (e.g. a pupil relay, or the like). By way of another example, the one or more illumination pathway lenses 114 may modify the diameter of the illumination beam 108.

In another embodiment, the inspection system 100 includes a sample stage 116 for securing and/or positioning the sample 102. The sample stage 116 may include any type of stage known in the art for positioning a sample 102 including, but not limited to, a linear translation stage, a rotational translation stage, or a translation stage with adjustable tip and/or tilt.

In another embodiment, the inspection system 100 includes a detector 118 configured to capture radiation emanating from the sample 102 through a collection pathway 120. For example, detector 118 may receive an image of the sample 102 provided by elements in the collection pathway 120. By way of another example, a detector 118 may receive radiation reflected, scattered (e.g., via specular reflection, diffuse reflection, and the like) or diffracted from the sample 102. By way of another example, a detector 118 may receive radiation generated by the sample 102 (e.g., luminescence generated by the absorption of the illumination beam 108, or the like). The collection pathway 120 may further include any number of optical elements to direct and/or modify illumination collected by the objective lens 104 including, but not limited to, one or more collection pathway lenses 122, one or more filters, one or more polarizers, or one or more beam blocks.

The detector 118 may include any type of optical detector known in the art suitable for measuring illumination received from the sample 102. For example, a detector 118 may include, but is not limited to, a CCD detector, a time delay integration (TDI) detector, a photomultiplier tube (PMT), an avalanche photodiode (APD), or the like. In another embodiment, a detector 118 may include a spectroscopic detector suitable for identifying wavelengths of radiation emanating from the sample 102.

In another embodiment, the inspection system 100 includes one or more field plane elements 124 located within a field plane. In this regard, the one or more field plane elements 124 may selectively modify one or more characteristics of radiation emanating from the sample based on the position from which the radiation emanates from the sample. For example, the one or more field plane elements 124 may include a field stop (e.g. an aperture, or the like) to reject stray light and/or mitigate ghost images on the detector 118. In another embodiment, the collection pathway lenses 122 may include a first collection pathway lens 122a to form an intermediate image of the sample 102 at a field plane for the placement of the field plane elements 124.

In another embodiment, the inspection system 100 includes one or more pupil plane elements 126 located within a pupil plane. In this regard, the one or more pupil plane elements 126 may selectively modify one or more characteristics of radiation emanating from the sample based on the angle at which the radiation emanates from the sample 102. For example, the one or more pupil plane elements 126 may include a phase plate to selectively modify the phase of radiation based on the angle at which the radiation emanates from the sample (e.g. for phase contrast imaging, or the like). By way of another example, the one or more pupil plane elements 126 may include a transmission filter to selectively modify the amplitude of radiation based on the angle at which the radiation emanates from the sample. In another embodiment, the collection pathway lenses 122 may include a second collection pathway lens 122b to form a relayed pupil plane for the placement of the pupil plane elements 126. In another embodiment, the collection pathway lenses 122 may include a third collection pathway lens 122c (e.g. a tube lens) to form an image of the sample 102 on the detector 118.

In one embodiment, as illustrated in FIG. 1A, the inspection system 100 may include a beamsplitter 128 oriented such that the objective lens 104 may simultaneously direct the illumination beam 108 to the sample 102 and collect radiation emanating from the sample 102. In another embodiment, though not shown, the collection pathway 120 may include separate elements. For example, the illumination pathway 110 may utilize a first focusing element to focus the illumination beam 108 onto the sample 102 and the collection pathway 120 may utilize a second focusing element to collect radiation from the sample 102. In this regard, the numerical apertures of the first focusing element and the second focusing element may be different. Further, it is noted herein that the inspection system 100 may facilitate multi-angle illumination of the sample 102, and/or more than one illumination source 106 (e.g. coupled to one or more additional detectors). In this regard, the inspection system 100 may perform multiple metrology measurements. In another embodiment, one or more optical components of the illumination pathway 110 and/or the collection pathway 120 may be mounted to a rotatable arm (not shown) pivoting around the sample 102 such that the angle of incidence of the illumination beam 108 on the sample 102 may be controlled by the position of the rotatable arm.

In another embodiment, the inspection system 100 includes a controller 130. In another embodiment, the controller 130 includes one or more processors 132 configured to execute program instructions maintained on a memory medium 134. In this regard, the one or more processors 132 of controller 130 may execute any of the various process steps described throughout the present disclosure. In another embodiment, the controller 130 is communicatively coupled to the detector 118. Accordingly, the controller 130 may receive collection signals from the detector 118 indicative of radiation emanating from the sample (e.g. reflected radiation, scattered radiation, or the like). For example, the one or more processors 132 of controller 130 may detect and/or classify defects based on defect scattering characteristics based on the collection signals.

The one or more processors 132 of a controller 130 may include any processing element known in the art. In this sense, the one or more processors 132 may include any microprocessor-type device configured to execute algorithms and/or instructions. In one embodiment, the one or more processors 132 may consist of a desktop computer, mainframe computer system, workstation, image computer, parallel processor, or any other computer system (e.g., networked computer) configured to execute a program configured to operate the inspection system 100, as described throughout the present disclosure. It is further recognized that the term "processor" may be broadly defined to encompass any device having one or more processing elements, which execute program instructions from a non-transitory memory medium 134. Further, the steps described throughout the present disclosure may be carried out by a single controller 130 or, alternatively, multiple controllers. Additionally, the controller 130 may include one or more controllers housed in a common housing or within multiple housings. In this way, any controller or combination of controllers may be separately packaged as a module suitable for integration into inspection system 100. Further, the controller 130 may analyze data received from the detector 118 and feed the data to additional components within the inspection system 100 or external to the inspection system 100.

The memory medium 134 may include any storage medium known in the art suitable for storing program instructions executable by the associated one or more processors 132. For example, the memory medium 134 may include a non-transitory memory medium. By way of another example, the memory medium 134 may include, but is not limited to, a read-only memory, a random access memory, a magnetic or optical memory device (e.g., disk), a magnetic tape, a solid state drive and the like. It is further noted that memory medium 134 may be housed in a common controller housing with the one or more processors 132. In one embodiment, the memory medium 134 may be located remotely with respect to the physical location of the one or more processors 132 and controller 130. For instance, the one or more processors 132 of controller 130 may access a remote memory (e.g., server), accessible through a network (e.g., internet, intranet and the like). Therefore, the above description should not be interpreted as a limitation on the present invention but merely an illustration.

Figure 2:
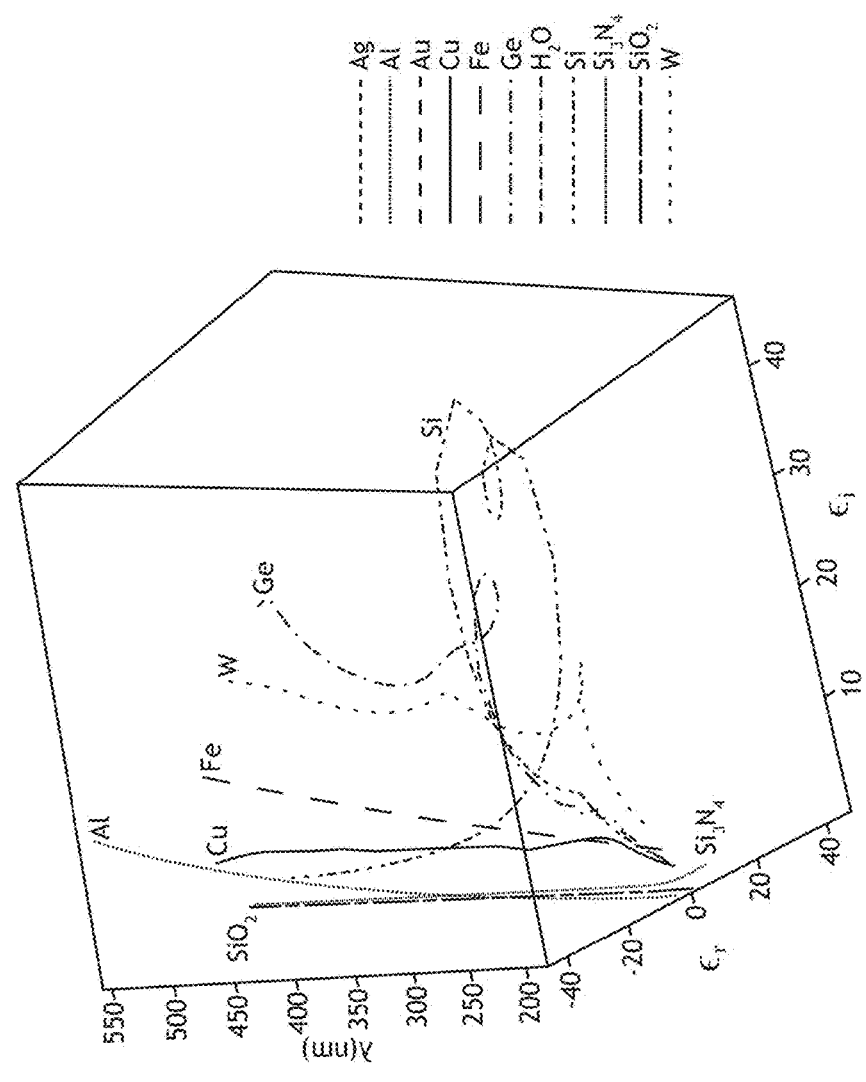
FIG. 2 is a plot of the complex relative permittivity as a function of wavelength for typical materials used in semiconductor manufacturing that may be associated with defects, in accordance with one or more embodiments of the present disclosure.

It is recognized herein that optical properties of a material are defined by its complex refractive index n or the complex relative permittivity $\varepsilon=\varepsilon_r-i\varepsilon_i=n^2$, where $\varepsilon_r$ and $\varepsilon_i$ are the real and imaginary parts of the relative permittivity, respectively. FIG. 2 is a plot 200 of the complex relative permittivity as a function of wavelength for typical, though not limiting, materials used in semiconductor manufacturing that may be associated with defects, in accordance with one or more embodiments of the present disclosure. As illustrated in FIG. 2, a dispersion curve representing the optical properties of a material as a function of wavelength is unique and may provide a basis for classifying the material composition of defects. However, classifying the material composition of defects based on the dispersion curve may not be practical or desirable in a production environment. For example, the sensitivity of the measurement may be limited by the usable spectral bandwidth for small particles as scattering signal drops rapidly (inversely to wavelength to the power of 4). By way of another example, variations in the scattering power as a function of wavelength may lead to further sensitivity reductions and/or reduced throughput associated with long measurement times.

Embodiments of the present disclosure are directed to the simultaneous detection and classification of defects based on defect scattering characteristics such as, but not limited to, scattering phase, scattering power, or defect absorption. Defect scattering characteristics provide sensitive metrics for classification of the material composition of defects and may be measured using a narrowband illumination source (e.g. a laser) for highly efficient utilization of energy from the illumination source. In this regard, embodiments of the present disclosure may provide high sensitivity in both defect detection and classification.

According to the Rayleigh model for elastic scattering by a small particle (e.g. a particle having a size much less than the wavelength of incident illumination), the scattering cross section is:

$$\sigma_s = \frac{128\pi^5}{3} \frac{a^6}{\lambda^4} \left| \frac{\epsilon - \epsilon_m}{\epsilon + 2\epsilon_m} \right|^2 \quad (1)$$

where a is the radius of the particle, λ is the wavelength of incident illumination (e.g. of the illumination beam 108, or the like), and ε and $\varepsilon_m$ are the relative permittivity of the defect and the surrounding media, respectively. It is recognized herein that both foreign particle defects and structural defects on a sample that scatter incident illumination may be treated as small particles that may scatter illumination.

The absorption cross section of such a small particle is:

$$\sigma_A = \frac{8\pi^2}{\lambda} a^3 \text{Im}\left( \frac{\epsilon - \epsilon_m}{\epsilon + 2\epsilon_m} \right). \quad (2)$$

Further, the phase of scattered light associated with a small particle:

$$\phi_s = \arg\left( \frac{\epsilon - \epsilon_m}{\epsilon + 2\epsilon_m} \right). \quad (3)$$

Equations (1)-(3) describe particle scattering and absorption in free space. For particles on a substrate (e.g. in the context of wafer inspection), the scattering and absorption cross sections are scaled by a factor (the q-factor) that takes into account coherent interaction of reflected field from substrate. However, the q-factor is independent of particle material properties and depends only on the substrate material properties. Therefore, the q-factor has a negligible effect on the relative phase shift between particles of different materials and may be ignored when considering the relative scattering phase of foreign particle defects. The effects of a substrate on Rayleigh scattering are generally described in Germer, *Applied Optics* 36 (33), 8798 (1997), which is incorporated herein by reference in its entirety.

Scattering characteristics may be used to classify the material composition of defects according to a variety of metrics and with a range of specificities. In one embodiment, defects may be classified based on identification of one or more elements and/or compounds within the defects. For example, one or more elements and/or compounds within a defect may be identified based on measurements of any combination of scattering characteristics (e.g., scattering phase, scattering power, defect absorption, or the like). In another embodiment, defects may be classified based on material type such as, but not limited to, metals, dielectrics, or organic materials. It may be the case that classification of defects by material type may be sufficient to adequately determine additional actions to be taken (e.g., discarding the wafer, exposing the wafer to additional cleaning steps based on the material type, identification of the locations of defects having different material type, or the like).

Further, samples in a production environment may be exposed to a limited number of known defect materials, which may reduce the number of scattering characteristics needed to classify a defect based on the material composition or the material type. For example, it may be the case that measuring a single scattering characteristic (e.g. either the scattering phase or the ratio of scattering power to defect absorption) may be sufficient to classify a defect within a known subset of materials or material types.

Figure 3:
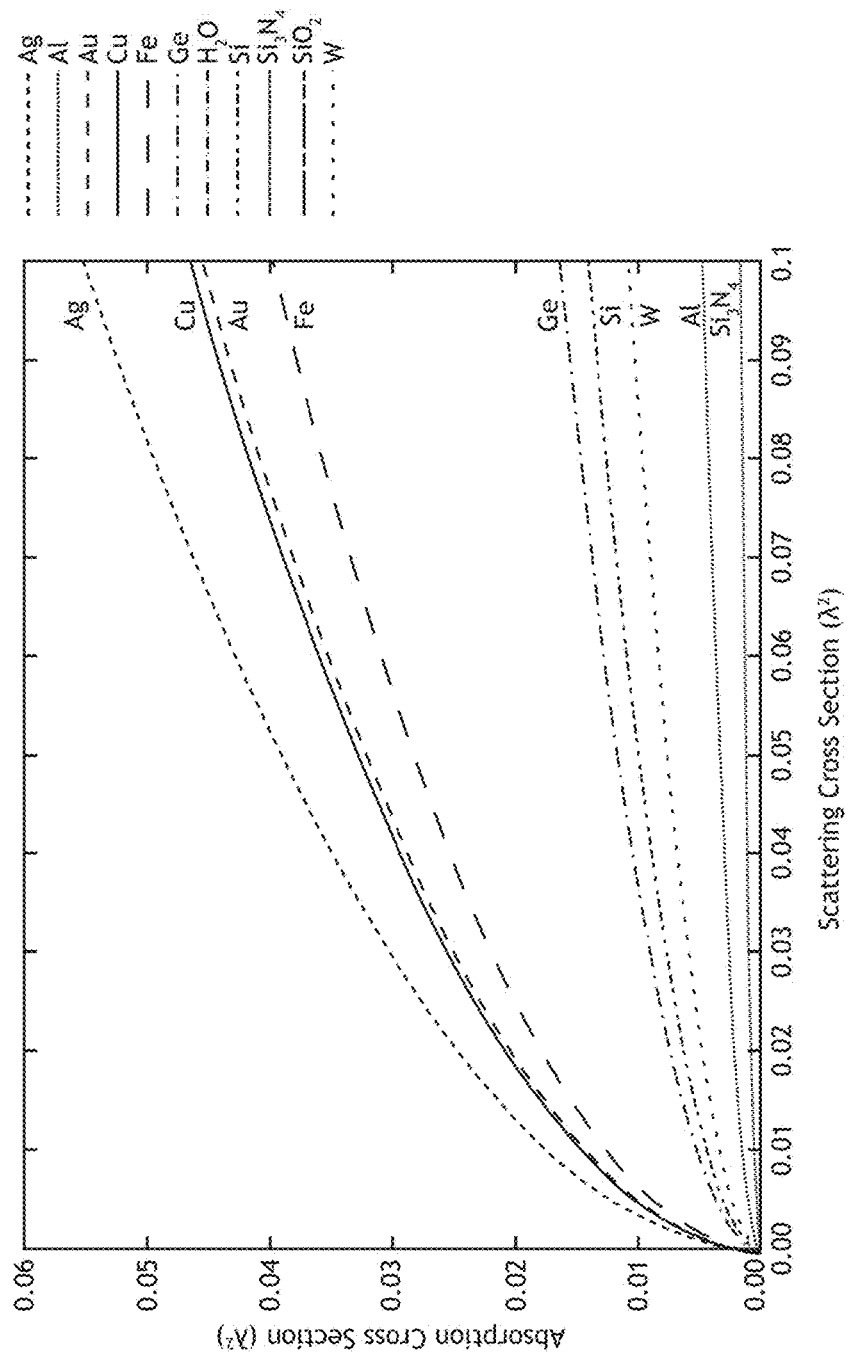
FIG. 3 is a plot of the absorption cross section as a function of the scattering cross section of particles at a wavelength of 266 nm for different particle sizes based on a Rayleigh scattering model, in accordance with one or more embodiments of the present disclosure.
Figure 4:
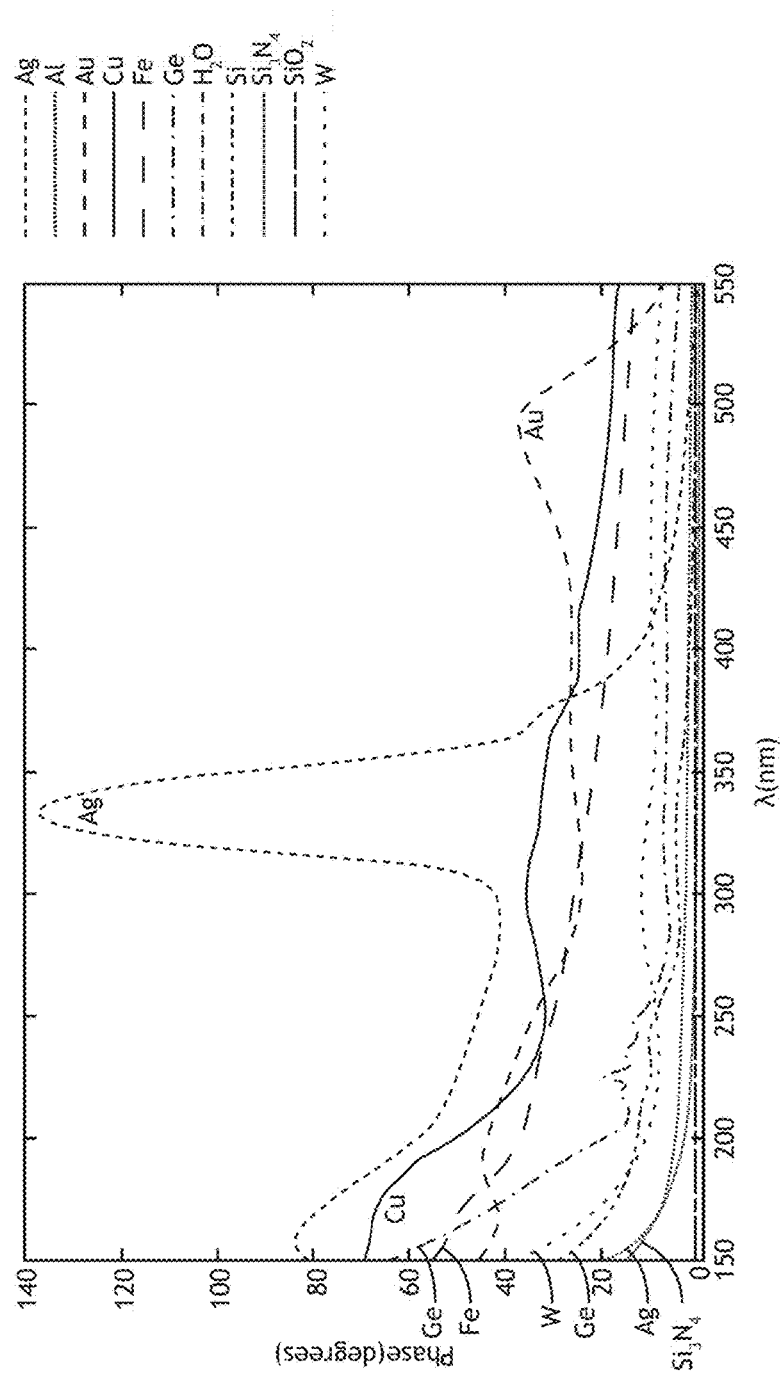
FIG. 4 is a plot of the scattering phase as a function of wavelength for various materials based on a Rayleigh scattering model, in accordance with one or more embodiments of the present disclosure.

FIGS. 3 and 4, as well as Table 1, provide exemplary data illustrating the classification of defects based on scattering characteristics in accordance with inventive concepts of the present disclosure. It is noted that the data included herein is provided solely for illustrative purposes and should not be interpreted as limiting the disclosure in any way.

FIG. 3 is a plot 300 of the absorption cross section as a function of the scattering cross section of particles at a wavelength of 266 nm for different particle sizes based on a Rayleigh scattering model, in accordance with one or more embodiments of the present disclosure. According to FIG. 3, different material types may be distinguished and classified based on the absorption and scattering cross-sections.

In one embodiment, defects are classified by material type based on absorption and scattering cross sections. For example, metals may have significantly stronger absorption than dielectric metals such that metals may be distinguished from dielectrics based on the absorption and scattering cross-sections. Further, as illustrated in FIG. 3, certain materials may have particularly large absorption cross sections that facilitate classification (e.g. silver (Ag), copper (Cu), gold (Au), or iron (Fe)).

In another embodiment, defects are classified by identifying a defect within a group of materials that have similar absorption and/or scattering cross sections. For example, utilizing the data of FIG. 3, defects may be classified into a first group of materials comprising silver (Ag), copper (Cu), gold (Au), or iron (Fe), a second group of materials comprising germanium (Ge), Silicon (Si), or Tungsten (W), and a third group of materials comprising silicon nitride ($Si_3N_4$), silicon dioxide ($SiO_2$), or water ($H_2O$). It is further noted that the groupings of materials included herein are provided solely for illustrative purposes and should not be interpreted to limit the present disclosure. In a general sense, defects may be classified based on any number of groupings of known materials.

In another embodiment, defects are classified by identifying with a high specificity the composition of at least one element and/or compound within a defect based on the absorption and/or scattering cross sections. The specificity to which a defect may be classified may be related to the sensitivity and/or accuracy of the measurement of scattering characteristics as well as the differences in scattering characteristics for known or expected contaminants.

FIG. 4 is a plot 400 of the scattering phase as a function of wavelength for various materials based on a Rayleigh scattering model, in accordance with one or more embodiments of the present disclosure. According to FIG. 4, materials may be distinguished and classified based on the scattering phase measured at any number of suitable wavelengths of illumination. For example, the value of the scattering phase is zero for dielectric materials having a real refractive index (e.g. $SiO_2$ in FIG. 4). Further, the values of the scattering phase for additional materials such as, but not limited to metals, may vary such that the material composition of defects may be determined by measuring the phase of illumination scattered by incident illumination. In one embodiment, defects may be classified based on measurement of scattering phase at a single wavelength. For example, scattering phase may be measured at a wavelength at which the values of the scattering phase of potential defects of interest may be distinguished. For instance, silver (Ag), copper (Cu), gold (Au) and iron (Fe) may exhibit values of scattering phase at a wavelength of 266 nm that are substantially higher than additional materials of interest such that these materials may be readily detected and classified. In another instance, the values of the scattering phase for many of the typical materials found in a semiconductor process may be readily distinguished at a wavelength of 193 nm.

Table 1 includes values of the relative permittivity, scattering cross section, absorption cross section, and scattering phase for 20 nm spheres of typical materials utilized in a semiconductor manufacturing process based on 266 nm illumination and a Rayleigh scattering model, in accordance with one or more embodiments of the present disclosure. Defects may be classified based on any combination of scattering characteristics. For example, Table 1 further illustrates that dielectrics may induce a relatively low scattered phase shift to incident illumination, whereas metals may induce a substantially higher scattered phase that may be readily measured for the purposes of defect detection and classification.

TABLE 1

Scattering characteristics for 20 nm spheres of various materials based on 266 nm illumination and a Rayleigh scattering model

| Material | $\epsilon_r$ | $\epsilon_i$ | Scattering Cross section | Absorption Cross section | Scattering Phase (deg) |
|---|---|---|---|---|---|
| Ag | 0.11 | 3.72 | 1.63E−04 | 6.02E−03 | 43.04 |
| Al | −10.04 | 1.38 | 3.80E−04 | 6.15E−04 | 2.62 |
| Au | −0.78 | 5.63 | 2.14E−04 | 5.02E−03 | 29.75 |
| Cu | −0.51 | 5.13 | 2.04E−04 | 5.33E−03 | 32.62 |
| Fe | −2.19 | 5.44 | 2.74E−04 | 5.43E−03 | 28.36 |
| Mo | −10.76 | 14.99 | 2.46E−04 | 1.47E−03 | 7.81 |
| W | 4.68 | 16.05 | 1.83E−04 | 1.57E−03 | 9.69 |
| Ge | −11.79 | 12.42 | 2.59E−04 | 1.47E−03 | 7.60 |
| Si | −16.21 | 16.18 | 2.45E−04 | 1.03E−03 | 5.48 |
| $Si_3N_4$ | 4.94 | 0.00 | 6.57E−05 | 2.36E−06 | 0.02 |
| $SiO_2$ | 2.25 | 0.00 | 1.76E−05 | 0.00E+00 | 0.00 |

Any number of scattering characteristics may be measured at any number of wavelengths to provide a desired level of specificity of classification. For example, a desired level of specificity may be reached by measuring one or more scattering characteristics at a single wavelength. By way of another example, a desired level of specificity may be reached by measuring a single scattering characteristic at one or more wavelengths. Further, additional measurement techniques such as, but not limited to, fluorescence imaging may be combined with the measurement of scattering characteristics to reach a desired level of specificity.

It is recognized herein that the description of scattering characteristics based on a Rayleigh scattering model provided in FIGS. 3 and 4, as well as in Table 1 are provided solely for illustrative purposes and should not be interpreted as limiting the present disclosure. While the Rayleigh scattering model may provide physical insights into scattering processes, scattering data generated by Rayleigh scattering models may have limitations. For example, metals having large values of negative real permittivity, $\epsilon_r$, and small values of imaginary permittivity, $\epsilon_i$, are known to have a scattering resonance associated with the excitation of localized surface plasmons that produces stronger scattering than predicted by a dipole-based Rayleigh scattering model alone. Surface plasmon resonance effects are generally described in Fan, et al., *Light: Science & Applications* 3, e179 (2014), which is incorporated herein by reference in its entirety.

In a general sense, reference data associated with classifying defects based on scattering characteristics may be obtained by any method known in the art. In another embodiment, scattering characteristics may be modeled through computational simulations (e.g. Finite Difference Time Domain (FDTD) simulations, or the like). In this regard, defects on a sample may be characterized based on a comparison of measured scattering characteristics with simulated scattering characteristics generated through the computational simulations. In a further embodiment, scattering characteristics of various defects with known size and composition may be measured to generate calibrated reference data. Accordingly, defects on a sample may be characterized based on a comparison of measured scattering characteristics with the calibration data.

In accordance with inventive concepts of the present disclosure, scattering characteristics of defects may be measured by multiple measurement techniques such as, but not limited to, interferometric techniques, imaging of the sample, or point-by-point scanning imaging techniques.

In one embodiment, defects are detected and classified based on illuminating a sample with an illumination beam, detecting radiation emanating from the sample (e.g. scattered and/or reflected radiation) using multiple detection modes, determining scattering characteristics based on the multiple detection modes, and classifying defects based on the scattering characteristics. Detection modes may include, but are not limited to, particular configurations of a phase plate in an interferometric measurement, the generation of a bright-field image, the generation of a dark-field image, or a measurement of the sample in a controlled immersion medium. In this regard, detecting radiation emanating from the sample with multiple detection modes may facilitate the measurement of one or more scattering characteristics of defects on the sample.

Referring generally to FIGS. 1A through 1F, the inspection system 100 may include a detection mode device 136 for modifying the detection mode of the inspection system 100.

In one embodiment, defects are detected and classified using phase contrast imaging. Phase contrast imaging may provide a stable common-path interferometer compatible with many image-based optical inspection tools. Accordingly, phase contrast imaging may be well-suited for production environments. Phase shifting phase contrast imaging is generally described in U.S. Pat. No. 7,295,303, granted on Nov. 13, 2007, which is incorporated herein by reference in its entirety.

In phase contrast imaging, the peak signal of particle scattering is given by the interference between specularly reflected light and scattered light:

$$P = P_{ref} + P_s + 2\sqrt{P_{ref}P_s}\cos(\phi_{ref} - \phi_s + \phi_0) \quad (4)$$

where $P_{ref}$ is the signal associated with reflected light, which may be considered as the reference arm of the interferometer, $P_s$ is the intensity of scattered light, $\phi_{ref}$ is the phase of reflected light common to all particles, $\phi_s$ is the phase of scattered light, $\phi_0$ is an adjustable phase shift between reflected light and scattered light.

Further, scattering characteristics associated with defects on a sample may be measured through phase shifting phase contrast imaging. In this regard, multiple collection signals are obtained corresponding to a series of measurements (e.g. associated with multiple detection modes) in which $\phi_0$ is varied by a known amount for each measurement.

N collection signals may be, but are not required to be, obtained in N measurements (e.g. N detection modes) where $\phi_0$ is varied in N equal phase steps within one phase cycle of $2\pi$. In this instance, the collection signal of a particle at each phase step may be described as:

$$P_n = P_{ref} + P_s + \sqrt{P_{ref}P_s}\cos\left[\delta\phi_s + (n-1)\frac{2\pi}{N}\right], \quad (5)$$

$$n = 1, 2, \ldots N,$$

where $\delta\phi_s = \phi_{ref} - \phi_s$ is the phase difference between scattered light and reflected light. The scattering phase may be extracted from the N collection signals according to:

$$\tan(\delta\phi_s) = \frac{A}{B}, \quad (6)$$

where $$A = \frac{2}{N}\sum_{n=1}^{N} P_n \sin\left(2\pi\frac{n-1}{N}\right), \text{ and} \quad (7)$$

$$B = \frac{2}{N}\sum_{n=1}^{N} P_n \cos\left(2\pi\frac{n-1}{N}\right). \quad (8)$$

In a case where N=4, equations (6)-(8) reduce to:

$$\tan(\delta\phi_s) = \frac{P_2 - P_4}{P_1 - P_3}. \quad (9)$$

In addition to the scattering phase, scattering power and absorption can be extracted from the N collection signals according to:

$$P_{ref} + P_s = \frac{1}{N}\sum_{n=1}^{N} P_n \quad (10)$$

and $$P_{ref}P_s = A^2 + B^2. \quad (11)$$

Further, the defect absorption is given by:

$$P_A = P_B - (P_{ref} + P_s) \quad (12)$$

Additionally, the scattering power and defect absorption may be written as $$P_s = I_0 \frac{128\pi^5}{3} \frac{a^6}{\lambda^4}(\alpha^2 + \beta^2) \quad (13)$$

and $$P_A = I_0 \frac{8\pi^2}{\lambda} a^3 \beta, \quad (14)$$

where $I_0$ is the intensity of the illumination beam 108 incident on the sample 102, $$\tan\phi_s = \frac{\beta}{\alpha}, \quad (15)$$

$$\alpha = \text{Re}\left\{\frac{\epsilon - \epsilon_m}{\epsilon + 2\epsilon_m}\right\}, \quad (16)$$

and $$\beta = \text{Im}\left\{\frac{\epsilon - \epsilon_m}{\epsilon + 2\epsilon_m}\right\}. \quad (17)$$

Accordingly, the scattering phase may also be obtained through:

$$\frac{P_A^2}{P_s^2} = \frac{3\lambda^2 I_0 \sin^2\phi_s}{2\pi}. \quad (18)$$

The relative phase shift between radiation specularly reflected by the sample and radiation scattered by the sample, $\phi_0$, may be adjusted by any technique known in the art to provide the N collection signals associated with N known values of the phase offset $\phi_0$.

In one embodiment, the detection mode device 136 of the inspection system 100 is configured to sequentially provide N different phase plates to a pupil plane of the inspection system 100 for the generation of N collection signals on the detector 118 associated with N different values of the phase offset $\phi_0$. In this regard, the N different phase plates may correspond to pupil plane elements 126 of the inspection system 100.

The N different phase plates may be physically located on different substrates or a common substrate. Further, the detection mode device 136 may provide the N different phase plates to the pupil plane by any method known in the art. In one embodiment (not shown), the detection mode device 136 includes a translation stage (e.g. a linear translation stage, a rotational translation stage, or the like) to translate the N phase plates to the pupil plane. In another embodiment (not shown), the detection mode device 136 may include a variable phase plate that may provide an adjustable phase shift as a function of position on the variable phase plate. In one instance, the variable phase plate may include a liquid crystal device. In another instance, the variable phase plate may include an electro-optical crystal that may introduce an adjustable phase shift controllable by an electric voltage.

Figure 1B:
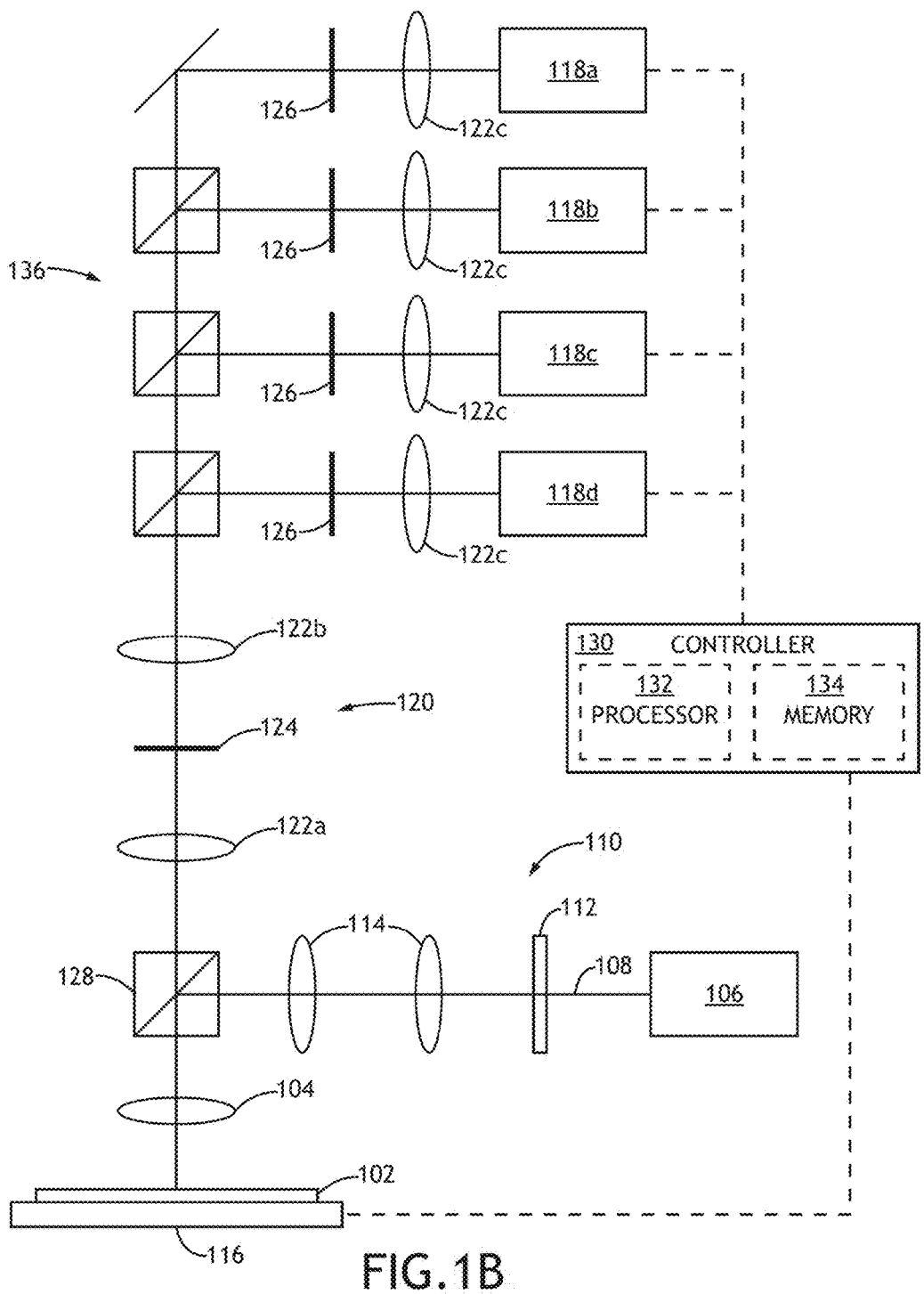
FIG. 1B is a conceptual view of an inspection system including four stationary phase plates, in accordance with one or more embodiments of the present disclosure.

In another embodiment, the detection mode device 136 may include a series of beamsplitters to split the radiation emanating from the sample 102 to N different beam paths. In this regard, the detection mode device 136 may provide a different stationary phase plate having a different phase offset $\phi_0$ to pupil planes of the N different beam paths. Further, the detector 118 may include a detector assembly located in each of the N different beam paths to provide N collection signals associated with the N different phase offsets $\phi_0$. FIG. 1B is a conceptual view of an inspection system 100 including four stationary phase plates, in accordance with one or more embodiments of the present disclosure. As illustrated in FIG. 1B, the detection mode device 136 may include beamsplitters to separate the radiation emanating from the sample to four beam paths including four phase plates in pupil planes of the four beam paths. In this regard, the phase plates may be pupil plane elements 126 of the system. Further, the four phase plates may provide four different known phase offsets $\phi_0$ (e.g. 0 degrees, 90 degrees, 180 degrees, and 270 degrees). In another embodiment, the detector 118 may include four detector assemblies 118a-118d located in the four beam paths to generate N collection signals associated with the N phase offsets $\phi_0$ for the detection and classification of defects.

Figure 1D:
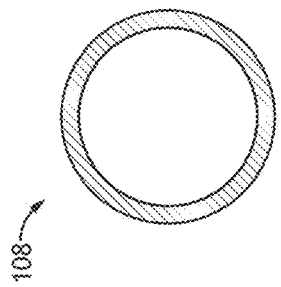
FIG. 1D is a conceptual view of an illumination beam with an annular profile for phase shifting phase contrast imaging, in accordance with one or more embodiments of the present disclosure.
Figure 1C:
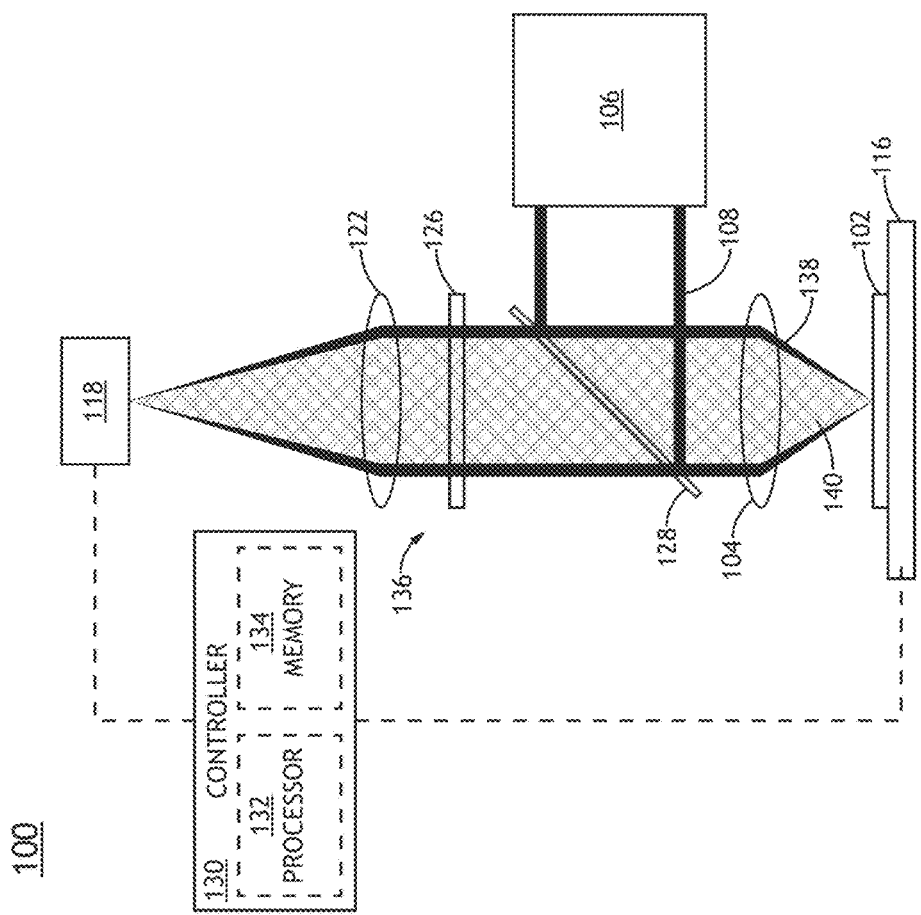
FIG. 1C is a conceptual view of an inspection system for phase shifting phase contrast imaging in which the relative phase of specularly reflected radiation and scattered radiation by the sample are controlled with phase plates, in accordance with one or more embodiments of the present disclosure.

FIG. 1C is a conceptual view of an inspection system 100 for phase shifting phase contrast imaging in which the relative phase of specularly reflected radiation 138 and scattered radiation 140 by the sample are controlled with phase plates, in accordance with one or more embodiments of the present disclosure.

In a general sense, a phase plate in a pupil plane may selectively modify the relative phase between specularly reflected and scattered radiation, $\phi_0$, if the specularly reflected and scattered radiation are at least partially distinguishable in the pupil plane. For example, the inspection system 100 may be configured to illuminate the sample 102 at a limited range of angles by limiting the distribution of the illumination beam 108 to select locations within the pupil plane of the objective lens 104 (e.g., the back focal plane of the objective lens 104). Specularly reflected radiation will then be limited to a complementary range of locations in the pupil plane, whereas scattered radiation may be present at any angle in the pupil plane. In this regard, a phase plate in a pupil plane may selectively modify the relative phase between specularly reflected and scattered radiation based on the positions of the specularly reflected and scattered radiation in the pupil plane. It is noted that although some scattered radiation may be affected by the phase plate, the impact on the measurements may be negligible.

The inspection system 100 may provide any distribution of the illumination beam 108 suitable for illuminating the sample 102 at a limited range of angles. For example, the inspection system 100 may provide an illumination beam with an annular profile, with one or more lobes, or the like. FIG. 1D is a conceptual view of an illumination beam with an annular profile for phase shifting phase contrast imaging, in accordance with one or more embodiments of the present disclosure. An annular profile may provide uniform radial illumination of the sample to avoid shadowing artifacts. Further, an annular profile near the edge of the numeric aperture (NA) of the objective lens 104 may provide the highest incident angles achievable by the objective lens 104, which may facilitate stronger scattering from defects and may be particularly beneficial for the detection and classification of small particles.

A desired distribution of the illumination beam 108 may be generated by any method known in the art. For example, the annular distribution illustrated in FIG. 1C may be, but is not required to be, generated directly by the illumination source 106, by a ring aperture to block unwanted light, by a diffractive optical element (DOE) to reshape illumination from the illumination source 106, a holographic diffuser to reshape illumination from the illumination source 106, or a fiber bundle arranged in an annular profile.

In another embodiment, one or more illumination pathway lenses 114 may relay a desired distribution of the illumination beam 108 to the back focal plane of the objective lens 104 to provide a desired range of illumination angles for the sample 102. Similarly, one or more collection pathway lenses 122 (e.g. 122b and/or 122a) may relay the back focal plane of the objective lens 104 to provide a relayed pupil plane suitable for the modification of the relative phase between specularly reflected radiation (e.g. specularly reflected radiation 138 of FIG. 1C) and scattered radiation (e.g. scattered radiation 140 of FIG. 1C) by phase plates.

The contrast of the interferometric signals provided by phase contrast imaging described in equations (4) and (5) may be proportional to the relative strengths of specularly reflected radiation (e.g. $P_{ref}$) and scattered radiation (e.g. $P_s$) at the detector 118. The strength of scattered radiation may be substantially lower than the strength of specularly reflected radiation, particularly for small particles. In another embodiment, the pupil plane elements 126 of the inspection system 100 include a transmission filter to reduce the strength of the specularly reflected radiation relative to the scattered radiation to facilitate high-contrast interferometric signals for sensitive particle detection and classification. For example, the transmission filter may be located proximate to any of the N phase plates provided by the detection mode device 136. By way of another example, a set of N transmission filters may be integrated into the N phase plates.

Referring still to FIG. 1C, in another embodiment, the inspection system 100 illuminates the sample 102 with an incoherent illumination beam 108 to avoid artifacts associated with imaging with coherent beams (e.g. speckle artifacts, or the like). In one instance, the illumination source 106 may directly provide an incoherent illumination beam 108. For example, the illumination source 106 may include an incoherent lamp illumination source. Further, the incoherent illumination source 106 may include a filter to control the output spectrum of the illumination beam 108. In another instance, the illumination source 106 may provide a coherent illumination beam 108 (e.g. a laser) and the inspection system 100 may include one or more elements to remove the coherence. For example, the one or more beam conditioning elements 112 may include a dynamic diffuser (e.g. a speckle buster).

In another embodiment, the beam conditioning elements 112 of the inspection system 100 include a polarizer for controlling the polarization of incident illumination on the inspection system 100. For example, the beam conditioning elements 112 may include a radial polarizer to provide consistent p-polarization for all azimuthal angles of illumination incident on the sample 102. It is recognized herein that the polarization state may be tuned based on expected types of defects to be detected and classified by the inspection system 100. Accordingly, the beam conditioning elements 112 may include any type of polarizer.

Figure 5:
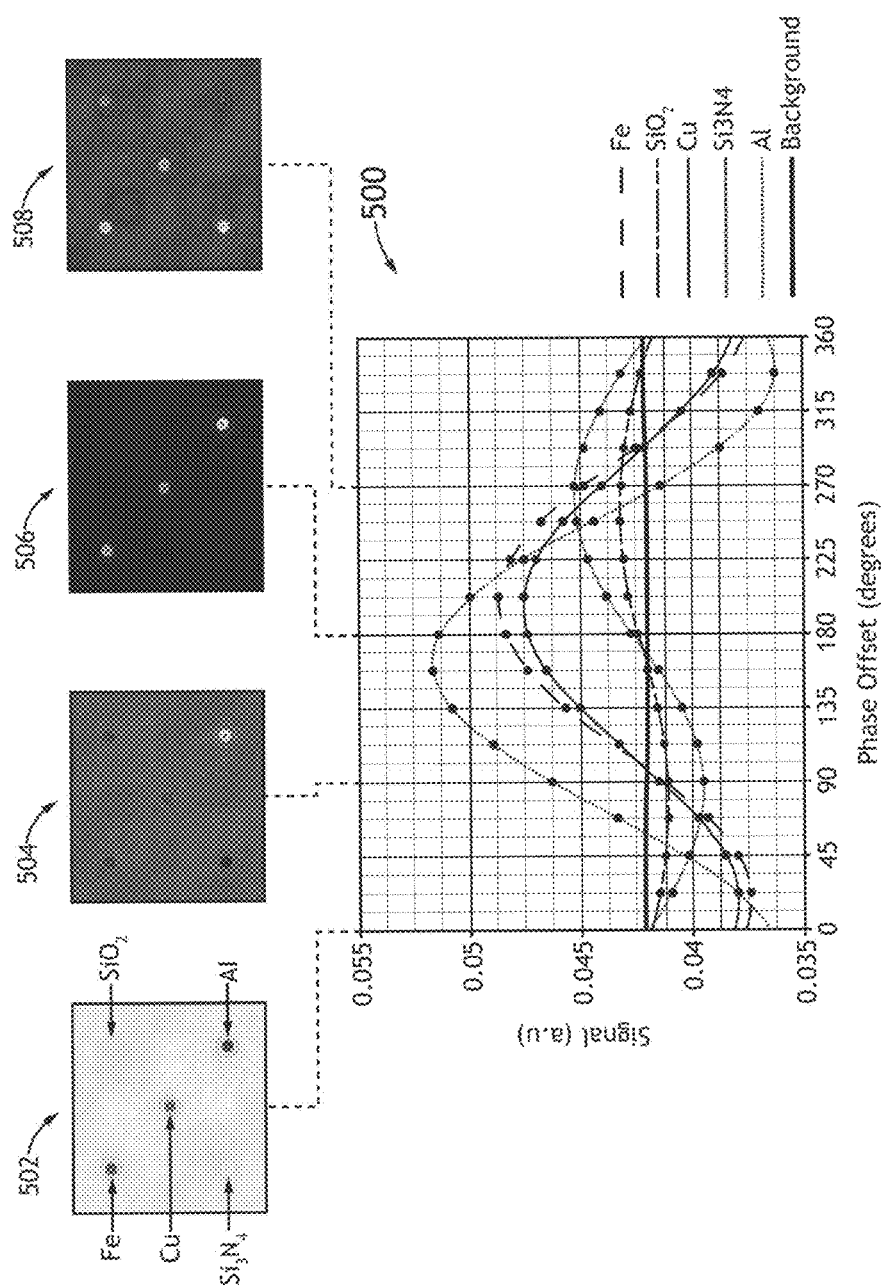
FIG. 5 includes a plot of FDTD simulations of phase shift phase contrast signals of 20 nm particles of various common foreign materials at a wavelength of 266 nm as a function of phase offset, in accordance with one or more embodiments of the present disclosure.

FIG. 5 includes a plot 500 of FDTD simulations of phase shift phase contrast signals of 20 nm particles of various common foreign materials at a wavelength of 266 nm as a function of phase offset (e.g. $\phi_0$), in accordance with one or more embodiments of the present disclosure. In particular, plot 500 includes FDTD simulations of phase shifting phase contrast signals of iron (Fe), silicon dioxide (SiO$_2$), copper (Cu), silicon nitride (Si$_3$N$_4$), and aluminum (Al) for 15 phase offsets $\phi_0$ (e.g. N=15). Further, plot 500 was simulated with an annular illumination beam with a center NA of 0.85 using a 0.9 NA objective lens and a 10% attenuation of specularly reflected radiation relative to scattered radiation. Plots 502-508 include images of the particles on the simulated sample at phase offsets of 0, 90, 180, and 270 degrees, respectively. As illustrated in plot 500, a series of phase shifting phase contrast signals generated with a series of known phase offsets between specularly reflected and scattered radiation provides an oscillatory signal for each material from which the scattered phase may be extracted. Notably, the relative phase shift between metals copper and iron compared to dielectrics silicon dioxide and silicon nitride are in good agreement with the calculations generated using the Rayleigh scattering model in Table 1. Further, the aluminum particle has a greater phase shift than predicted by the Rayleigh scattering model due to excitation of localized surface plasmons predicted by the FDTD simulations.

Referring again to FIG. 1A, in one embodiment, the phase offset $\phi_0$ between specularly reflected and scattered radiation may additionally be controlled by varying the focal position of the sample stage 116 along an optic axis of the objective lens 104. In this regard, the detection mode device 136 may include the sample stage 116 such that the detection mode device 136 may control the focal position of the sample 102. The phase offset due to defocus may be described as a function of the imaging pupil position:

$$\phi_0 = \frac{2\pi}{\lambda} z(1 - \cos\theta), \quad (19)$$

where z is defocus (e.g. a variation of the position of the sample from a nominal focal position) and sin θ is the normalized pupil radius. The phase offset of scattered light may further be approximated as:

$$\varphi_0 = \frac{2\pi}{\lambda} z(\cos\theta_s - \cos\theta_r), \quad (20)$$

where $\theta_r$ is the polar angle of specularly reflected radiation and $\theta_s$ represents a weighted average of polar angles of scattered radiation collected by the objective lens 104.

Figure 6:
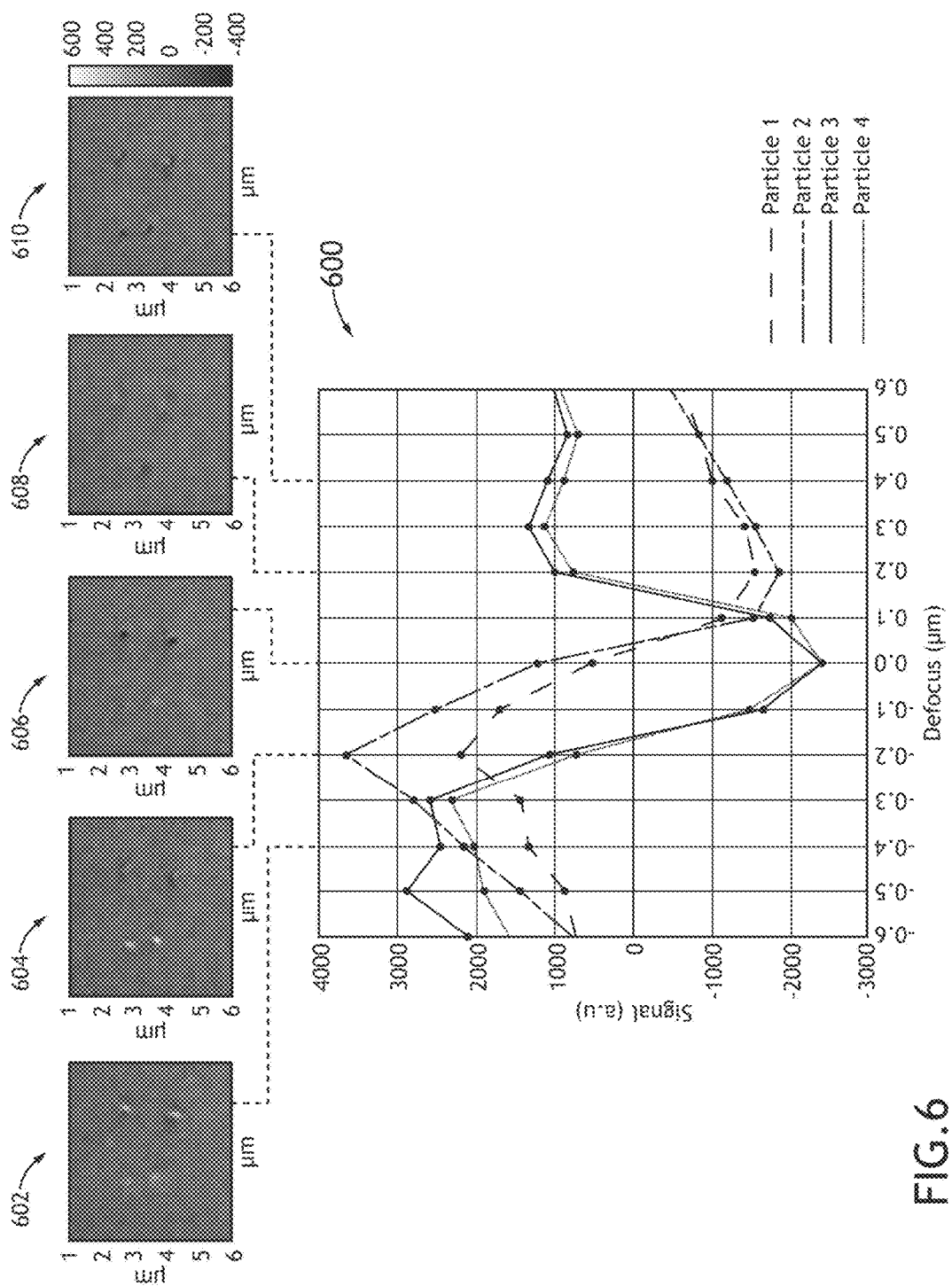
FIG. 6 is a plot of measured phase shifting phase contrast signals of 100 nm particles of various common foreign materials as a function of sample focal position, in accordance with one or more embodiments of the present disclosure.

FIG. 6 is a plot 600 of measured phase shifting phase contrast signals of 100 nm particles of various common foreign materials as a function of sample focal position, in accordance with one or more embodiments of the present disclosure. In particular, plot 600 includes measured phase shifting phase contrast signals associated with two 100 nm gold (Au) spheres and two 100 nm silicon dioxide (SiO$_2$) spheres for 13 values of the sample position (e.g. N=13) using laser illumination at a wavelength of 266 nm. Further, plot 600 was generated with an annular illumination beam with a NA ranging from 0.75 to 0.85 using a 0.85 NA objective lens. Plots 602-610 include phase shifting phase contrast images of the measured spheres on the sample at defocus values of −0.4 µm, −0.2 µm, 0 µm, 0.2 µm, and 0.4 µm, respectively. As illustrated in plot 600, a series of phase shifting phase contrast signals generated with a series of known phase offsets between specularly reflected and scattered radiation (e.g. generated by adjusting the focal position of the sample) provides an oscillatory signal for each material from which the scattered phase may be extracted. FIG. 6 clearly illustrates a substantial difference between the scattered phase of the gold particles and the silicon dioxide spheres such that phase shifting phase contrast imaging may detect and classify defects.

Figure 7:
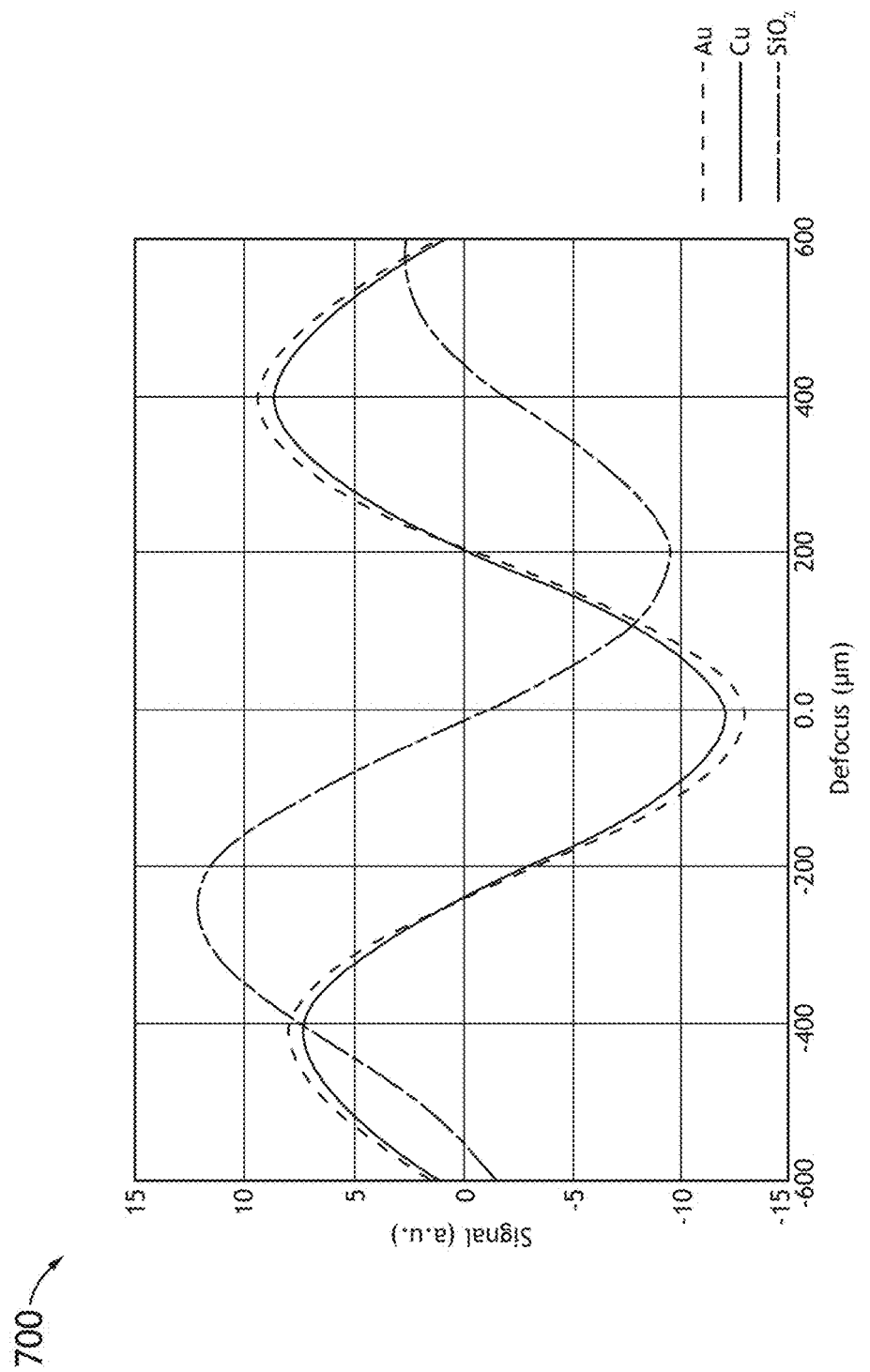
FIG. 7 is a plot including FDTD simulations of 100 nm particles of gold, silicon dioxide, and copper under the same conditions as for data illustrated in FIG. 6, in accordance with one or more embodiments of the present disclosure.

FIG. 7 is a plot 700 including FDTD simulations of 100 nm particles of gold, silicon dioxide, and copper under the same conditions as for data illustrated in FIG. 6, in accordance with one or more embodiments of the present disclosure. A comparison of plots 600 and 700 reveals a good correlation between measurements and simulated data. In this regard, phase shifting phase contrast imaging may detect and distinguish defects formed from different materials. Accordingly, phase shifting phase contrast imaging signals may be used to classify defects according to material type or material composition.

Figure 1F:
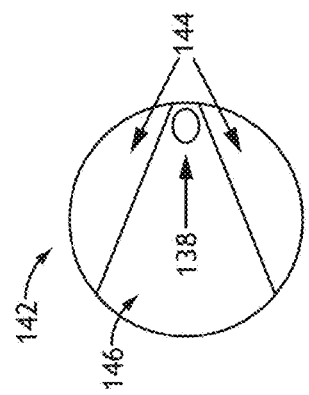
FIG. 1F is a simplified schematic of a polarizer mask, in accordance with one or more embodiments of the present disclosure.
Figure 1E:
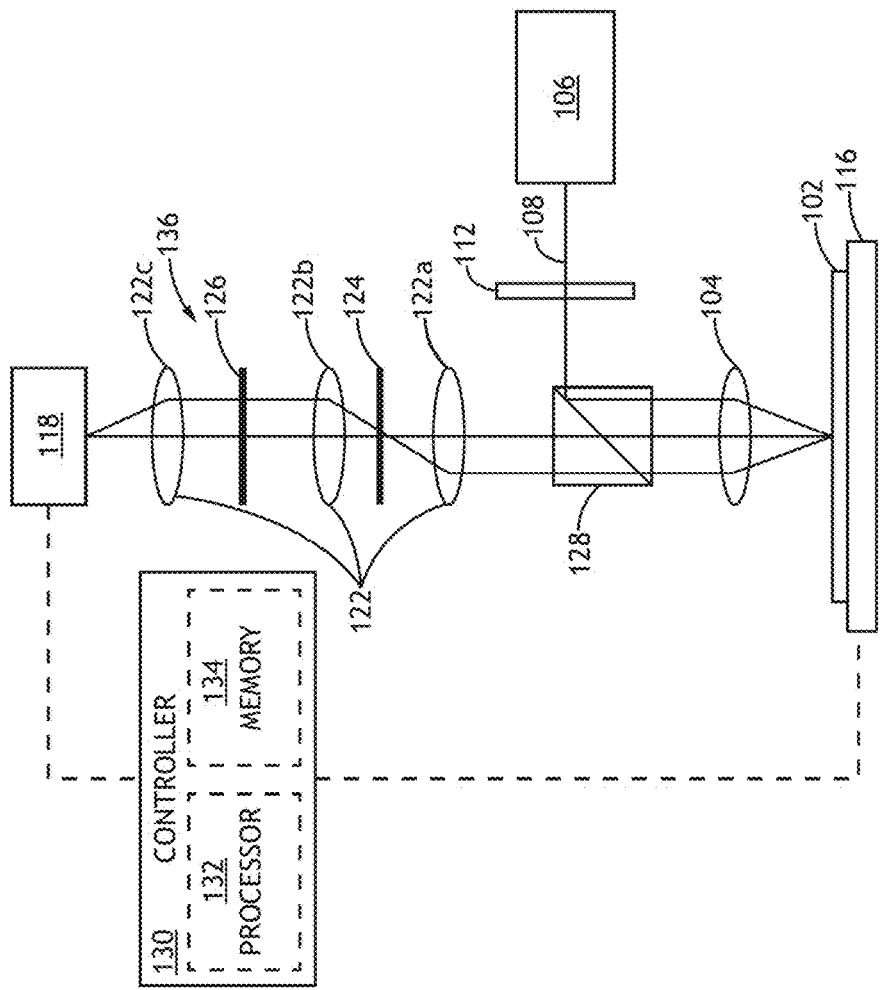
FIG. 1E is a conceptual view of an inspection system for phase shifting phase contrast imaging using coherent illumination, in accordance with one or more embodiments of the present disclosure.

Referring now to FIGS. 1E and 1F, phase shifting phase contrast imaging may be employed in a coherent imaging system. FIG. 1E is a conceptual view of an inspection system 100 for phase shifting phase contrast imaging using coherent illumination, in accordance with one or more embodiments of the present disclosure. In one embodiment, the inspection system 100 provides at least one collimated illumination beam 108 to an off-axis position of the back focal plane of the objective lens 104 such that the illumination beam 108 is incident on the sample 102 at a high NA. A pupil plane of the collection pathway 120 will thus include at least one collimated beam associated with specularly reflected radiation at limited locations of the pupil plane and scattered radiation at any other position within the pupil plane. Accordingly, a detection mode device 136 may provide a series of N phase masks introducing N known values of a phase offset $\phi_0$ between the specularly reflected and scattered radiation. For example, as previously described, the detection mode device 136 may sequentially translate the N phase masks to a pupil plane. By way of another example, as previously described, the detection mode device 136 may include a series of beamsplitters to split radiation emanating from the sample 102 into N beam paths for parallel detection of N collection signals associated with N values of $\phi_0$. It is noted herein that simultaneous measurement of multiple phase shifting phase contrast signals in this manner may provide highly efficient throughput for defect detection and classification.

In another embodiment, one or more TDI imaging sensors are used to detect the one or more phase shifting phase contrast signals to provide line-scan images of the sample and associated defects. The illumination source 106 of FIG. 1E may further generate an incoherent illumination beam 108 as coherent imaging artifacts (e.g. speckle artifacts) may be negligent in point-by-point imaging configurations.

In another embodiment, the pupil plane elements 126 of the inspection system 100 may include polarizer masks to suppress scattering from the surface of the sample. In this regard, polarizer masks may increase the detection sensitivity of phase shifting phase contrast imaging to small particles. It is recognized herein that the polarizations of various components of radiation emanating from the sample (e.g. specularly reflected radiation, radiation scattered by defects, and radiation scattered by the sample, or the like) may be different from each other and may further vary across the NA of the objective lens 104. Accordingly, the collection pathway 120 may include a polarizer (e.g. a linear polarizer having a constant polarization direction across the NA, a mirror symmetric polarizer having two different polarization directions symmetrically distributed across the NA, or the like) and a polarizer mask configured to selectively transmit one or more desired components of radiation emanating from the sample. The use of polarizer masks to suppress surface scattering is generally described in U.S. Pat. No. 8,891,079, granted on Nov. 18, 2014, and U.S. Patent Application No. 2016/0097727, published on Apr. 7, 2016, both of which are incorporated herein by reference in its entirety.

FIG. 1F is a simplified schematic of a polarizer mask 142, in accordance with one or more embodiments of the present disclosure. In one embodiment, the polarizer mask 142 includes transmissive regions 144 and blocking regions 146. Further, the blocking regions 146 may include one or more attenuated transmission regions at which a portion of the specularly reflected radiation 138 may pass. Accordingly, specularly reflected radiation 138 and the scattered radiation 140 associated with defect scattering (not shown) may be transmitted, whereas radiation scattered by the surface of the sample (e.g. constituting noise in a phase shifting phase contrast measurement) may be blocked.

Referring again generally to FIG. 1A, the inspection system 100 may measure scattering characteristics including scattering power and defect absorption without measuring the scattering phase. Such measurements may be used for the detection and classification of defects alone, or in combination with measurements of the scattering phase as described previously herein.

In one embodiment, defects are detected and classified based on measurements of the scattering power and defect absorption associated with bright-field and dark-field images of a sample. For example, the inspection system 100 may provide a bright-field image using any distribution of illumination beam 108 and an open (e.g. non-obstructed or minimally-obstructed) pupil plane. The signal strength associated with each point of a bright-field image may thus correspond to the reflectivity of the corresponding portion of the sample and the signal strength associated with the defect may be related to light loss due to absorption. In this regard, a bright-field image (or its inverse) may provide measurements of the absorption cross section of defects on the sample.

In contrast, a dark-field image may be obtained using complementary distributions of the illumination beam 108 and a mask in the pupil plane. In this regard, specularly reflected radiation from the sample is blocked in the pupil plane and scattered radiation is transmitted in the pupil plane. Accordingly, the signal strength associated with the defect may correspond to the scattering power of the defect.

In another embodiment, the detection mode device 136 of the inspection system 100 sequentially modifies the transmissivity of the pupil plane to provide a bright-field image as a bright-field collection signal and a dark-field image as a dark-field collection signal for the detection and classification of defects. For example, the inspection system 100 may provide a fixed illumination beam 108 suitable for both bright-field and dark-field detection modes (e.g. an annular distribution, single or multi-lobed distribution, or the like). Further, the detection mode device 136 may sequentially provide an open aperture and a blocking aperture complementing the distribution of the illumination beam 108 such that the detector 118 may provide bright-field and dark-field collection signals for the detection and classification of defects based on scattering power and defect absorption.

The bright-field and dark-field apertures may be physically located on different substrates or a common substrate. Further, the detection mode device 136 may provide the bright-field and dark-field apertures to the pupil plane by any method known in the art. In one embodiment (not shown), the detection mode device 136 includes a translation stage (e.g. a linear translation stage, a rotational translation stage, or the like) to translate the apertures to the pupil plane. In another embodiment (not shown), the detection mode device 136 may include a variable aperture that may provide an adjustable transmissivity as a function of position on the variable aperture. In one instance, the variable phase plate may include a liquid crystal device.

In another embodiment, the detection mode device 136 may modify both the transmissivity of the pupil plane and the distribution of the illumination beam 108 to provide bright-field and dark-field detection modes. For example, the detection mode device 136 may provide an aperture to a pupil plane of the illumination pathway 110 for modification of the distribution of the illumination beam 108 and an aperture to a pupil plane of the collection pathway 120 to modify the transmission of radiation emanating from the sample to the detector 118.

In one embodiment, defects are detected and classified based on a comparison of multiple images of the sample in which the refractive index of the immersion medium surrounding the sample is modified. The scattering cross section of a defect and thus the power of a scattering signal may vary based on the refractive index of the immersion medium and particularly on the difference between the refractive index of the defect and the immersion medium. A ratio of Rayleigh scattering cross sections of common defect materials in water immersion and dry imaging modes at 193 nm and 266 nm is provided in Table 2, in accordance with one or more embodiments of the present disclosure.

TABLE 2

Ratio of scattering cross section in water immersion and dry imaging modes for wavelengths of 193 nm and 266 nm

|  | 193 nm | 266 nm |
| --- | --- | --- |
| Al | 22.57 | 1.93 |
| Cu | 0.70 | 0.86 |
| Au | 0.60 | 0.90 |
| Fe | 0.86 | 1.07 |
| Ge | 1.35 | 1.24 |
| Si | 1.92 | 1.18 |
| $Si_3N_4$ | 0.43 | 0.37 |
| $SiO_2$ | 0.02 | 0.03 |
| W | 1.48 | 0.90 |

As illustrated in Table 2, defects may be classified based on the ratio of scattering power measured with water immersion and dry immersion. In particular, metal particles may be distinguished from dielectrics or weakly absorbing materials. For example, the real refractive index of many dielectrics (e.g. $SiO_2$) may be substantially closer to water than that of many metals (e.g. Al, Au, or the like) such that the ratio of scattering cross sections in water immersion and dry imaging may be substantially lower for dielectrics than for metals.

In another embodiment, the detection mode device 136 of the inspection system 100 sequentially modifies the immersion medium surrounding the sample to include two or more immersion media with known refractive indices. In this regard, the detector 118 may generate two or more collection signals associated with imaging the sample in the two or more immersion media. The immersion media may be liquid (e.g. water, immersion oil, or the like) or gaseous (open atmosphere, nitrogen, argon, or the like). For example, the detection mode device 136 may include a chamber to contain the sample and an immersion medium. Further, the detection mode device 136 may include immersion media transfer devices such as, but not limited to, reservoirs, tubing, pumps, valves, or pressure regulators.

Tables 3 and 4 provide experimental measurements of the scattering power of 100 nm spheres of gold and silicon dioxide in dark-field water immersion and dry imaging modes with annular illumination at a wavelength of 266 nm, in accordance with one or more embodiments of the present disclosure.

TABLE 3

Scattering power of 100 nm gold spheres in water immersion and dry imaging modes

| Particle # | Water Immersion | Dry Imaging | Ratio |
| --- | --- | --- | --- |
| 1 | 2151 | 4091 | 0.53 |
| 2 | 2825 | 7125 | 0.40 |
| 3 | 2464 | 5184 | 0.48 |
| 4 | 2934 | 6726 | 0.44 |
| 5 | 2264 | 3318 | 0.68 |
| 6 | 2621 | 5565 | 0.47 |
| 7 | 3036 | 8551 | 0.36 |
| 8 | 2539 | 5572 | 0.46 |
| 9 | 2492 | 4513 | 0.55 |
| Average | 2592 | 5627 | 0.46 |

TABLE 4

Scattering power of 100 nm silicon dioxide spheres in water immersion and dry imaging modes

| Particle # | Water Immersion | Dry Imaging | Ratio |
| --- | --- | --- | --- |
| 1 | 1101 | 30567 | 0.04 |
| 2 | 1168 | 31986 | 0.04 |
| 3 | 1236 | 35392 | 0.03 |
| 4 | 1091 | 28697 | 0.04 |
| 5 | 1188 | 37896 | 0.03 |
| 6 | 1388 | 40767 | 0.03 |
| 7 | 1133 | 31135 | 0.04 |
| 8 | 1470 | 45609 | 0.03 |
| 9 | 1203 | 35893 | 0.03 |
| 10 | 1028 | 28380 | 0.04 |
| 11 | 1253 | 40650 | 0.03 |
| 12 | 1350 | 39365 | 0.03 |
| 13 | 1315 | 36627 | 0.04 |
| 14 | 1349 | 42303 | 0.03 |
| Average | 1234 | 36091 | 0.03 |

A comparison of experimental data of Tables 3 and 4 with simulated data in Table 2 reveals that the measured data is in good agreement with the simulations. Accordingly, defects may be readily classified based on a comparison of scattering power measured with multiple imaging modes, where each imaging mode corresponds to an image in a different immersion medium.

Figure 8:
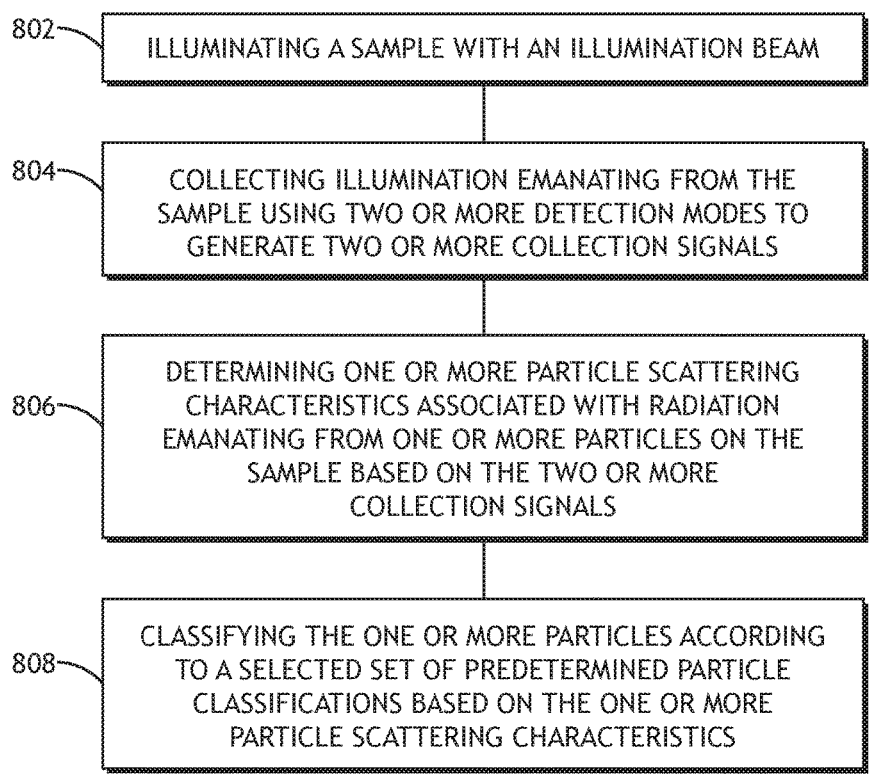
FIG. 8 is a flow diagram illustrating steps performed in a method for detecting and classifying defects based on defect scattering characteristics, in accordance with one or more embodiments of the present disclosure.

FIG. 8 is a flow diagram illustrating steps performed in a method 800 for detecting and classifying defects based on defect scattering characteristics, in accordance with one or more embodiments of the present disclosure. Applicant notes that the embodiments and enabling technologies described previously herein in the context of system 100 should be interpreted to extend to method 800. It is further noted, however, that the method 800 is not limited to the architecture of inspection system 100.

In one embodiment, method 800 includes a step 802 of illuminating a sample with an illumination beam. The illumination beam may include any wavelength of illumination including, but not limited to, VUV, DUV, UV, visible, or IR wavelengths. Further, the illumination beam may be spatially coherent or spatially incoherent. For example, a spatially coherent beam (e.g. a laser source, or the like) may provide highly efficient use of spectral power in point-by-point imaging. By way of another example, a spatially incoherent beam (e.g. a lamp source, a speckle-busted laser source, or the like) may illuminate an extended portion of the sample for extended imaging.

Illumination of the sample may induce the sample to emanate radiation. For example, upon illumination by the illumination beam, a sample may reflect (e.g. specularly reflect) radiation, scatter radiation (e.g. by one or more defects), and/or diffract radiation. It is recognized herein that diffracted radiation from a sample may be indicative of the frequencies of features on the sample such that small features may generate higher diffraction orders than relatively larger features within a given solid angle.

In one embodiment, step 802 includes illuminating the sample at an angle (e.g. a high NA, or the like) such that one or more non-zero diffraction orders of radiation may emanate from the sample.

In another embodiment, method 800 includes a step 804 of collecting illumination from the sample using two or more detection modes to generate two or more detection signals. In another embodiment, method 800 includes a step 806 of determining one or more defect scattering characteristics associated with radiation emanating from the sample based on the two or more collection signals. In another embodiment, method 800 includes a step 808 of classifying one or more defects based on one or more scattering characteristics associated with defects on the sample.

Defect scattering characteristics may include, but are not limited to, scattering phase, scattering power, and defect absorption. In a general sense, the scattering characteristics will vary based on the composition of the defect. Accordingly, the composition of defect may be determined through measurement of the defect scattering characteristics. Further, defects may be classified based on the measured defect scattering characteristics. For example, defects may be classified based on the identification of one or more elements and/or compounds within a defect or by a generic material type (e.g. metals, dielectrics, organics, or the like) based on the sensitivity of the measurements. It may be the case that a known set of materials may be known or commonly expected to be present as defects. In such cases, the limited number of materials may decrease the required measurement sensitivity to classify defects according to a desired granularity.

In one embodiment, defect scattering characteristics associated with one or more defects on the sample are determined based on measurements using a narrowband illumination source. In another embodiment, short wavelength illumination (e.g. VUV wavelengths, DUV wavelengths, UV wavelengths, or the like) are utilized by method 800 to provide high scattering power and efficient use of spectral power of the illumination source based on a $\lambda^{-4}$ dependence of scattering power on wavelength.

For example, step 804 may include the collection of radiation emanating from the sample using multiple detection modes to provide at least the scattering phase associated with defects on the sample.

In one embodiment, step 804 includes the measurement of multiple phase contrast images of a sample to provide phase shifting phase contrast imaging based in interference between specularly reflected and scattered radiation from the sample. A step 804 may then include intentionally introducing a series of known phase offsets between the specularly reflected and scattered illumination and generating a phase contrast interference image for each known phase offset. A step 806 may then include determining any of the scattered phase, the scattered power, and/or the defect absorption associated with defects on the sample based off of the series of phase contrast images. Further, step 808 may include classifying defects on the sample based on the scattered phase, scattered power, and/or defect absorption. Additionally, the detection of the multiple collection signals associated with the known phase offsets introduced in phase shifting phase contrast imaging may be performed sequentially or simultaneously.

In another embodiment, step 804 includes measurement of at least a bright-field image and a dark-field image of the sample. A step 806 may then include a determination of the scattered power and/or the defect absorption associated with defects on the sample based on the at least the bright-field and dark-field images. For example, a bright-field image may provide the absorption of defects on the sample (e.g. the absorption cross-section), while a dark-field image may provide the scattering power of the sample (e.g. the scattering cross-section). A step 808 may then include classifying defects based on the scattering power and/or the defect absorption.

In another embodiment, step 804 includes measurement of the sample surrounded by at least two different immersion media (e.g., ambient atmosphere, water, immersion oil, or the like). The scattering power of a defect may be a function of a difference between the refractive index of the immersion medium. In step 806, the scattering cross section (based on the scattering power) may be measured for each medium. Accordingly, a ratio of a measured scattering cross section of a defect measured in two different immersion media may be calculated in step 808 to classify defects.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically interactable and/or physically interacting components and/or wirelessly interactable and/or wirelessly interacting components and/or logically interactable and/or logically interacting components.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A system, comprising:
    an illumination source configured to generate an illumination beam;
    one or more focusing lenses configured to direct the illumination beam to a sample;
    a detector;
    one or more collection lenses configured to direct radiation emanating from the sample to the detector, wherein the radiation emanating from the sample includes radiation specularly reflected by the sample and radiation scattered by the sample;
    one or more phase plates configured to introduce two or more different selected phase offsets between the radiation specularly reflected by the sample and the radiation scattered by the sample such that the detector generates two or more collection signals; and
    a controller communicatively coupled to the detector, the controller including one or more processors configured to execute program instructions configured to direct the one or more processors to:
        determine one or more scattering phase values introduced to the illumination beam scattered by one or more defects on the sample based on the two or more collection signals; and classify the one or more defects according to a set of predetermined defect classifications based on the one or more scattering phase values.

2. The system of claim 1, wherein the one or more phase plates comprise:
two or more phase plates mounted on a translation stage communicatively coupled to the controller, wherein the translation stage is configured to sequentially insert the two or more phase plates into the radiation emanating from the sample to introduce the two or more selected phase offsets, wherein the two or more collection signals correspond to two or more signals sequentially generated by the detector in response to the radiation emanating from the sample modified by the two or more phase plates.

3. The system of claim 1, further comprising:
one or more beamsplitters to separate the radiation emanating from the sample into two or more sample beams, wherein the one or more phase plates comprise:
two or more phase plates, wherein the two or more sample beams are directed to the two or more phase plates to introduce the two or more selected phase offsets, wherein the two or more collection signals correspond to two or more signals generated by two or more detector assemblies of the detector in response to the radiation emanating from the sample modified by the two or more phase plates.

4. The system of claim 1, wherein the one or more phase plates comprise:
a translation stage to secure the sample, wherein the translation stage is communicatively coupled to the controller, wherein the translation stage is configured to translate the sample to two or more focal positions along an optical axis of the one or more focusing lenses to introduce the two or more different selected phase offsets, wherein the two or more collection signals correspond to two or more signals generated by the detector at the two or more focal positions.

5. The system of claim 1, further comprising:
one or more apertures configured to sequentially create a bright-field image on the detector as a first collection signal of the two or more collection signals based on the radiation emanating from the sample and a dark-field image on the detector as a second collection signal of the two or more collection signals based on the radiation emanating from the sample.

6. The system of claim 1, wherein at least a first one of the two or more collection signals comprise:
a dry image, wherein at least one of the two or more collection signals comprises:
a water immersion image.

7. The system of claim 1, further comprising:
an attenuation plate configured to reduce the intensity of illumination specularly reflected by the sample relative to illumination scattered by the sample.

8. The system of claim 1, wherein the set of predetermined defect classifications comprises:
at least one of metals, dielectrics, or organic materials.

9. The system of claim 1, wherein the set of predetermined defect classifications comprises:
at least one of silver, aluminum, gold, copper, iron, molybdenum, tungsten, germanium, silicon, silicon nitrate, or silicon dioxide.

10. The system of claim 1, wherein the radiation emanating from the sample further includes fluorescent radiation, wherein the one or more processors are further configured to:

determine one or more fluorescent intensity values associated with illumination generated by one or more defects on the sample based on the two or more collection signals; and
classify the one or more defects according to a set of predetermined defect classifications based on the one or more fluorescent intensity values.

11. The system of claim 1, wherein the illumination beam comprises:
an annular illumination beam.

12. The system of claim 11, wherein the illumination beam comprises:
a spatially incoherent illumination beam.

13. The system of claim 11, wherein the illumination source comprises:
a narrowband illumination source.

14. The system of claim 13, wherein the illumination source comprises:
a speckle-busted laser source.

15. The system of claim 11, wherein the illumination source comprises:
a broadband illumination source.

16. The system of claim 15, wherein the broadband illumination source comprises:
an incoherent lamp source.

17. The system of claim 15, wherein the broadband illumination source comprises:
a tunable broadband illumination source.

18. The system of claim 11, wherein the illumination beam comprises:
a spatially coherent illumination beam.

19. The system of claim 18, wherein the illumination beam comprises:
a laser source.

20. The system of claim 19, wherein the laser source comprises:
a tunable laser source.

21. The system of claim 1, wherein the system further includes a polarizer mask in a pupil plane of the one or more collection lenses configured to suppress illumination scattered by a surface of the sample with respect to illumination scattered by the one or more defects on the sample.

22. The system of claim 21, wherein the illumination beam comprises:
a single collimated illumination beam.

23. The system of claim 21, wherein the detector comprises:
a time delay and integration (TDI) detector.

24. The system of claim 1, wherein the one or more focusing lenses and the one or more collection lenses share at least one common lens.

25. The system of claim 1, wherein the one or more phase plates comprises:
a variable phase plate mounted on a translation stage communicatively coupled to the controller, wherein the translation stage is configured to sequentially modify a position of the variable phase plate with respect to the radiation emanating from the sample to introduce the two or more selected phase offsets, wherein the two or more collection signals correspond to two or more signals sequentially generated by the detector in response to the radiation emanating from the sample modified by the variable phase plate.

26. A system, comprising:
an illumination source configured to generate an illumination beam;

one or more focusing elements configured to direct the illumination beam to a sample;
a detector;
one or more collection elements configured to direct radiation emanating from the sample to the detector, wherein the radiation emanating from the sample includes radiation specularly reflected by the sample and radiation scattered by the sample;
a translation stage to secure the sample, wherein the translation stage is configured to translate the sample to two or more focal positions along an optical axis of the one or more focusing lenses to introduce two or more different selected phase offsets between the radiation specularly reflected by the sample and the radiation scattered by the sample such that the detector generates two or more collection signals at the two or more focal positions; and
a controller communicatively coupled to the detector and the translation stage, the controller including one or more processors configured to execute program instructions configured to direct the one or more processors to:
  determine one or more scattering phase values introduced to the illumination beam scattered by one or more defects on the sample based on the two or more collection signals; and
  classify the one or more defects according to a set of predetermined defect classifications based on the one or more scattering phase values.

27. A system, comprising:
an illumination source configured to generate an illumination beam;
one or more focusing lenses configured to direct the illumination beam to a sample;
a detector;
one or more collection lenses configured to direct radiation emanating from the sample to the detector, wherein the radiation emanating from the sample includes radiation specularly reflected by the sample and radiation scattered by the sample;
a detection mode control device configured to sequentially create a bright-field image on the detector based on the radiation emanating from the sample as a bright-field collection signal and a dark-field image on the detector based on the radiation emanating from the sample as a dark-field collection signal; and
a controller communicatively coupled to the detector, the controller including one or more processors configured to execute program instructions configured to direct the one or more processors to:
  compare the bright-field collection signal and the dark-field collection signal to detect one or more defects on the sample;
  determine defect absorption values for the one or more defects based on signal strengths of the one or more defects in the bright-field collection signal;
  determine scattering intensity values for the one or more defects based on signal strengths of the one or more defects in the dark-field collection signal; and
  classify the one or more defects according to a set of predetermined defect classifications based on the defect absorption values and the scattering intensity values of the one or more defects.

28. A system, comprising:
an illumination source configured to generate an illumination beam;
one or more focusing lenses configured to direct the illumination beam to a sample;
a detector;
one or more collection lenses configured to direct radiation emanating from the sample to the detector, wherein the radiation emanating from the sample includes radiation specularly reflected by the sample and radiation scattered by the sample;
a chamber configured to contain the sample and an immersion medium; and
a controller communicatively coupled to the detector, the controller including one or more processors configured to execute program instructions configured to direct the one or more processors to:
  receive a dry collection signal from the detector generated with the immersion medium including a gas;
  receive an immersion collection signal from the detector generated with the immersion medium including a liquid;
  compare the dry collection signal and the immersion collection signal to detect one or more defects on the sample; and
  classify the one or more defects according to a set of predetermined defect classifications based on the comparison of the dry collection signal and the immersion collection signal.

29. A method for defect classification, comprising:
illuminating a sample with an illumination beam;
collecting illumination emanating from the sample using two or more detection modes, wherein the radiation emanating from the sample includes radiation specularly reflected from the sample and radiation scattered from the sample;
introducing two or more different selected phase offsets between the radiation specularly reflected by the sample and the radiation scattered by the sample to generate two or more collection signals;
determining one or more defect scattering phase values introduced to the illumination beam scattered by one or more defects on the sample based on the two or more collection signals; and
classifying the one or more defects according to a selected set of predetermined defect classifications based on the one or more scattering phase values.

* * * * *